(12) United States Patent
Lu et al.

(10) Patent No.: US 8,401,148 B2
(45) Date of Patent: Mar. 19, 2013

(54) NON-VOXEL-BASED BROAD-BEAM (NVBB) ALGORITHM FOR INTENSITY MODULATED RADIATION THERAPY DOSE CALCULATION AND PLAN OPTIMIZATION

(75) Inventors: Weiguo Lu, Madison, WI (US); Mingli Chen, Madison, WI (US); Quan Chen, Madison, WI (US); Kenneth J. Ruchala, Madison, WI (US)

(73) Assignee: Tomotherapy Incorporated, Madison, WI (US)

( * ) Notice: Subject to any disclaimer, the term of this patent is extended or adjusted under 35 U.S.C. 154(b) by 245 days.

(21) Appl. No.: 12/915,618

(22) Filed: Oct. 29, 2010

(65) Prior Publication Data

US 2011/0122997 A1   May 26, 2011

Related U.S. Application Data

(60) Provisional application No. 61/256,593, filed on Oct. 30, 2009, provisional application No. 61/295,462, filed on Jan. 15, 2010.

(51) Int. Cl.
*A61N 5/10* (2006.01)
(52) U.S. Cl. .......................................... 378/65
(58) Field of Classification Search .................... 378/65
See application file for complete search history.

(56) References Cited

U.S. PATENT DOCUMENTS

| 4,149,081 A | 4/1979 | Seppi |
| 4,455,609 A | 6/1984 | Inamura et al. |
| 4,998,268 A | 3/1991 | Winter |
| 5,008,907 A | 4/1991 | Norman et al. |
| 5,044,354 A | 9/1991 | Goldhorn et al. |
| 5,065,315 A | 11/1991 | Garcia |
| 5,117,829 A | 6/1992 | Miller et al. |
| 5,317,616 A | 5/1994 | Swerdloff et al. |
| 5,332,908 A | 7/1994 | Weidlich |
| 5,335,255 A | 8/1994 | Seppi et al. |
| 5,351,280 A | 9/1994 | Swerdloff et al. |
| 5,391,139 A | 2/1995 | Edmundson |
| 5,394,452 A | 2/1995 | Swerdloff et al. |
| 5,405,309 A | 4/1995 | Carden, Jr. |
| 5,442,675 A | 8/1995 | Swerdloff et al. |

(Continued)

FOREIGN PATENT DOCUMENTS

| JP | 10052421 | 2/1998 |
| JP | 10501151 | 2/1998 |

(Continued)

OTHER PUBLICATIONS

Purdy, James, "3D Treatment Planning and Intensity-Modulated Radiation Therapy," Oncology, vol. 13, No. 10, suppl. 5 (Oct. 1999).

(Continued)

*Primary Examiner* — Glen Kao
(74) *Attorney, Agent, or Firm* — Michael Best & Friedrich LLP

(57) ABSTRACT

A method of calculating a dose distribution for a patient for use in a radiation therapy treatment plan. The method includes acquiring an image of a volume within the patient, defining a radiation source, and defining a reference plane oriented between the radiation source and the patient. The method also includes generating a radiation therapy treatment plan, wherein the plan includes a plurality of rays that extend between the radiation source and the patient volume, and calculating a three-dimensional dose volume for the patient volume from the plurality of rays that intersect the reference plane without first having to independently calculate a dose distribution on each of the plurality of rays. The method can also include displaying the three-dimensional dose volume.

32 Claims, 14 Drawing Sheets

U.S. PATENT DOCUMENTS

| | | | |
|---|---|---|---|
| 5,446,548 A | 8/1995 | Gerig et al. | |
| 5,471,516 A | 11/1995 | Nunan | |
| 5,511,549 A | 4/1996 | Legg et al. | |
| 5,528,650 A | 6/1996 | Swerdloff et al. | |
| 5,548,627 A | 8/1996 | Swerdloff et al. | |
| 5,552,605 A | 9/1996 | Arata | |
| 5,579,358 A | 11/1996 | Lin | |
| 5,596,619 A | 1/1997 | Carol | |
| 5,596,653 A | 1/1997 | Kurokawa | |
| 5,621,779 A | 4/1997 | Hughes et al. | |
| 5,622,187 A | 4/1997 | Carol | |
| 5,625,663 A | 4/1997 | Swerdloff et al. | |
| 5,647,663 A | 7/1997 | Holmes | |
| 5,651,043 A | 7/1997 | Tsuyuki et al. | |
| 5,661,773 A | 8/1997 | Swerdloff et al. | |
| 5,668,371 A | 9/1997 | Deasy et al. | |
| 5,673,300 A | 9/1997 | Reckwerdt et al. | |
| 5,692,507 A | 12/1997 | Seppi et al. | |
| 5,712,482 A | 1/1998 | Gaiser et al. | |
| 5,724,400 A | 3/1998 | Swerdloff et al. | |
| 5,751,781 A | 5/1998 | Brown et al. | |
| 5,754,622 A | 5/1998 | Hughes | |
| 5,754,623 A | 5/1998 | Seki | |
| 5,760,395 A | 6/1998 | Johnstone | |
| 5,802,136 A | 9/1998 | Carol | |
| 5,818,902 A | 10/1998 | Yu | |
| 5,823,192 A | 10/1998 | Kalend et al. | |
| 5,835,562 A | 11/1998 | Ramsdell et al. | |
| 6,038,283 A | 3/2000 | Carol et al. | |
| 6,049,587 A | 4/2000 | Leksell et al. | |
| 6,222,905 B1 | 4/2001 | Yoda et al. | |
| 6,241,670 B1 | 6/2001 | Nambu | |
| 6,260,005 B1 | 7/2001 | Yang et al. | |
| 6,301,329 B1 | 10/2001 | Surridge | |
| 6,360,116 B1 | 3/2002 | Jackson, Jr. et al. | |
| 6,385,286 B1 | 5/2002 | Fitchard et al. | |
| 6,385,288 B1 | 5/2002 | Kanematsu | |
| 6,393,096 B1 | 5/2002 | Carol et al. | |
| 6,438,202 B1 | 8/2002 | Olivera et al. | |
| 6,473,490 B1 | 10/2002 | Siochi | |
| 6,527,443 B1 | 3/2003 | Vilsmeier et al. | |
| 6,539,247 B2 | 3/2003 | Spetz | |
| 6,560,311 B1 | 5/2003 | Shepard et al. | |
| 6,661,870 B2 | 12/2003 | Kapatoes et al. | |
| 6,697,452 B2 | 2/2004 | Xing | |
| 6,714,620 B2 | 3/2004 | Caflisch et al. | |
| 6,719,683 B2 | 4/2004 | Frohlich | |
| 6,741,674 B2 | 5/2004 | Lee | |
| 6,757,355 B1 | 6/2004 | Siochi | |
| 6,792,073 B2 | 9/2004 | Deasy et al. | |
| 6,792,074 B2 | 9/2004 | Erbel et al. | |
| 6,853,702 B2 * | 2/2005 | Renner | 378/65 |
| 6,882,702 B2 | 4/2005 | Luo | |
| 6,904,125 B2 | 6/2005 | Van Dyk et al. | |
| 6,961,405 B2 | 11/2005 | Scherch | |
| 6,984,835 B2 | 1/2006 | Harada | |
| 7,043,058 B2 | 5/2006 | Cornog et al. | |
| 7,046,762 B2 | 5/2006 | Lee | |
| 7,187,752 B2 | 3/2007 | Kotler et al. | |
| 7,221,733 B1 | 5/2007 | Takai et al. | |
| 7,289,599 B2 | 10/2007 | Seppi et al. | |
| 7,367,955 B2 | 5/2008 | Zhang et al. | |
| 7,369,645 B2 | 5/2008 | Lane | |
| 7,391,026 B2 | 6/2008 | Trinkaus et al. | |
| 7,450,687 B2 | 11/2008 | Yeo et al. | |
| 7,492,858 B2 | 2/2009 | Partain et al. | |
| 7,496,173 B2 | 2/2009 | Goldman et al. | |
| 7,505,559 B2 | 3/2009 | Kuduvalli | |
| 7,508,967 B2 | 3/2009 | Harari et al. | |
| 7,513,861 B2 | 4/2009 | Klein et al. | |
| 7,519,150 B2 | 4/2009 | Romesberg et al. | |
| 7,551,717 B2 | 6/2009 | Tome et al. | |
| 7,590,440 B2 | 9/2009 | Lu et al. | |
| 7,620,144 B2 | 11/2009 | Bodduluri | |
| 7,639,853 B2 | 12/2009 | Olivera et al. | |
| 7,639,854 B2 | 12/2009 | Schnarr et al. | |
| 7,643,661 B2 | 1/2010 | Ruchala et al. | |
| 7,693,257 B2 | 4/2010 | Allison | |
| 7,708,682 B2 | 5/2010 | Pekar et al. | |
| 7,773,788 B2 | 8/2010 | Lu et al. | |
| 7,831,289 B2 | 11/2010 | Riker et al. | |
| 7,945,022 B2 | 5/2011 | Nelms et al. | |
| 8,085,899 B2 | 12/2011 | Nord et al. | |
| 8,125,813 B2 | 2/2012 | Nizin et al. | |
| 2003/0212325 A1 | 11/2003 | Cotrutz et al. | |
| 2004/0068182 A1 | 4/2004 | Misra | |
| 2005/0096515 A1 | 5/2005 | Geng | |
| 2005/0143965 A1 | 6/2005 | Failla et al. | |
| 2005/0201516 A1 | 9/2005 | Ruchala et al. | |
| 2007/0041496 A1 | 2/2007 | Olivera et al. | |
| 2007/0041498 A1 | 2/2007 | Olivera et al. | |
| 2007/0041500 A1 | 2/2007 | Olivera et al. | |
| 2007/0197908 A1 | 8/2007 | Ruchala et al. | |
| 2008/0008291 A1 | 1/2008 | Alakuijala et al. | |
| 2008/0031406 A1 | 2/2008 | Yan et al. | |
| 2008/0049896 A1 * | 2/2008 | Romesberg et al. | 378/65 |
| 2008/0193006 A1 | 8/2008 | Udupa et al. | |
| 2008/0279328 A1 | 11/2008 | Zeitler et al. | |
| 2009/0041200 A1 | 2/2009 | Lu et al. | |
| 2009/0116616 A1 | 5/2009 | Lu et al. | |
| 2009/0252291 A1 | 10/2009 | Lu et al. | |
| 2010/0053208 A1 | 3/2010 | Menningen et al. | |
| 2010/0054413 A1 | 3/2010 | Sobering et al. | |
| 2011/0019889 A1 | 1/2011 | Gering et al. | |

FOREIGN PATENT DOCUMENTS

| | | |
|---|---|---|
| JP | 10146395 | 6/1998 |
| JP | 11169471 | 6/1999 |
| JP | 2002210029 | 7/2002 |
| JP | 2002522128 | 7/2002 |
| JP | 2002522129 | 7/2002 |
| JP | 2004166975 | 6/2004 |
| JP | 2005160804 | 6/2005 |
| JP | 2005518908 | 6/2005 |
| JP | 2007509644 | 4/2007 |
| JP | 2007516743 | 6/2007 |
| TW | 300853 | 3/1997 |
| WO | 0007669 | 2/2000 |
| WO | 03076003 | 9/2003 |
| WO | 03092789 | 11/2003 |
| WO | 2004080522 | 9/2004 |
| WO | 2004098712 | 11/2004 |
| WO | 2005031629 | 4/2005 |
| WO | 2005057463 | 6/2005 |
| WO | 2005062790 | 7/2005 |

OTHER PUBLICATIONS

Yu, Cedric X., et al., "A Method for Implementing Dynamic Photon Beam Intensity Modulation using Independent Jaws and a Multileaf Collimator," Phys. Med. Biol. 40. 1995: 769-787.

Lee, Jason et al., "Intensity Modulated Radiation Therapy; An Introduction for Patients and Clinicians," www.oncolink.com/templates/treatment/article.cfm?c=45&s=33&id=182; Jun. 16, 2001.

Keall, Paul, "4-Dimensional Computed Tomography Imaging and Treatment Planning," Seminars in Radiation Oncology, vol. 14, No. 1, Jan. 2004; pp. 81-90.

Rueckert, D. et al., "Nonrigid Registration Using Free-Form Deformations: Application to Breast MR Images", IEEE Transactions on Medical Imaging, vol. 18, No. 8, pp. 712-721, Aug. 1999.

Gu et al. GPU-based ultra-fast dose calculation using a finite size pencil beam model. Physics in Medicine and Biology. Oct. 1, 2009, vol. 54, No. 20, pp. 6287-6297.

Mackie, T. Rockwell et al., "Tomotherapy: Rethinking the Processes of Radiotherapy," XIIth ICCR, May 27-30, 1997.

Fang, Guang Y. et al., "Software system for the UW/GE tomotherapy prototype," Xiith ICCR, May 27-30, 1997.

PCT/US2010/054758 International Search Report and Written Opinion dated Aug. 2, 2011.

* cited by examiner

NON-VOXEL-BASED BROAD-BEAM (NVBB) ALGORITHM FOR INTENSITY MODULATED RADIATION THERAPY DOSE CALCULATION AND PLAN OPTIMIZATION

RELATED APPLICATIONS

This application is a non-provisional application of and claims priority to U.S. Provisional Patent Application Ser. No. 61/256,593, filed on Oct. 30, 2009, and U.S. Provisional Patent Application Ser. No. 61/295,462, filed on Jan. 15, 2010, the entire contents of which are both incorporated herein by reference.

FIELD OF THE INVENTION

Embodiments of the invention relate to a radiation therapy imaging and treatment system. More specifically, embodiments of the invention relate to methods and systems for performing non-voxel-based broad-beam dose calculation for intensity modulated radiation therapy optimization.

BACKGROUND OF THE INVENTION

Medical equipment for radiation therapy treats tumorous tissue with high energy radiation. In external source radiation therapy, a radiation source external to the patient treats internal tumors. The external source is normally collimated to direct a beam only to the tumor location. Typically, the radiation source consists of either high-energy X-rays, electrons from certain linear accelerators, or gamma rays from highly focused radioisotopes.

The dose and the placement of the dose must be accurately controlled to insure both that the tumor receives sufficient radiation to be destroyed and that damage to the surrounding and adjacent non-tumorous tissue is minimized. To properly plan and perform a radiation therapy treatment session, tumors and adjacent normal structures can be delineated in three-dimensions using specialized hardware and software. For example, intensity modulated radiation therapy ("IMRT") treats a patient with multiple rays of radiation each of which may be independently controlled in intensity and/or energy. The rays are directed from different angles about the patient and combine to provide a desired dose pattern. The desired dose pattern is determined and optimized based on the three-dimensional shape of the tumorous tissue.

Conventional IMRT optimization, however, has some costs. For example, IMRT optimization generally requires the use of sophisticated, expensive hardware and software. In addition, the computer processing required for IMRT optimization can be time-consuming, such that full treatment planning and optimization cannot be performed under time constraints. Approximations may be used to increase the processing time of IMRT optimization, but these can reduce the accuracy of the optimization. Furthermore, conventional IMRT optimization only accounts for beamlet parameters or voxel parameters and fails to take other parameters, such as machine parameters, into account.

SUMMARY OF THE INVENTION

Accordingly, embodiments of the invention provide systems and methods for non-voxel, broad-beam based dose calculation for IMRT optimization. The method enables direct optimization of machine parameters, such as dynamic jaw optimization, leaf position, and angle selections, by using continuous viewpoint and functional formulation. The method also adopts non-voxel-based representation, which makes the optimization flexible and efficient. The systems and methods can also use graphics processing units to further increase optimization processing time and accuracy.

In particular, embodiments of the invention provide a method of calculating a dose distribution for a patient for use in a radiation therapy treatment plan. The method includes acquiring an image of a volume within the patient, defining a radiation source, and defining a reference plane oriented between the radiation source and the patient. The method also includes generating a radiation therapy treatment plan that includes a plurality of rays that extend between the radiation source and the patient volume and calculating a three-dimensional dose volume for the patient volume from the plurality of rays that intersect the reference plane without first having to independently calculate a dose distribution on each of the plurality of rays. The method can also include displaying the three-dimensional dose volume.

Embodiments of the invention also provide a method of optimizing a dose distribution for a patient for use in a radiation therapy treatment plan. The method includes (a) acquiring an image of a volume within the patient, (b) generating a radiation therapy treatment plan, the plan including a plurality of rays that extend between a radiation source and the patient volume, (c) generating an initial set of machine parameters, and (d) calculating a three-dimensional dose volume based on the initial set of machine parameters and the patient volume, the calculation further based on the plurality of rays that intersect the reference plane without first having to independently calculate a dose distribution on each of the plurality of rays. Furthermore, the method includes (e) evaluating an objective functional based on the three-dimensional dose volume, (f) calculating a first derivative of the objective functional, and (g) updating the initial set of machine parameters based on the objective functional. The method also includes (h) repeating acts (d) through (g) at least one time.

Other aspects of the invention will become apparent by consideration of the detailed description and accompanying drawings.

DETAILED DESCRIPTION

Figure 1:
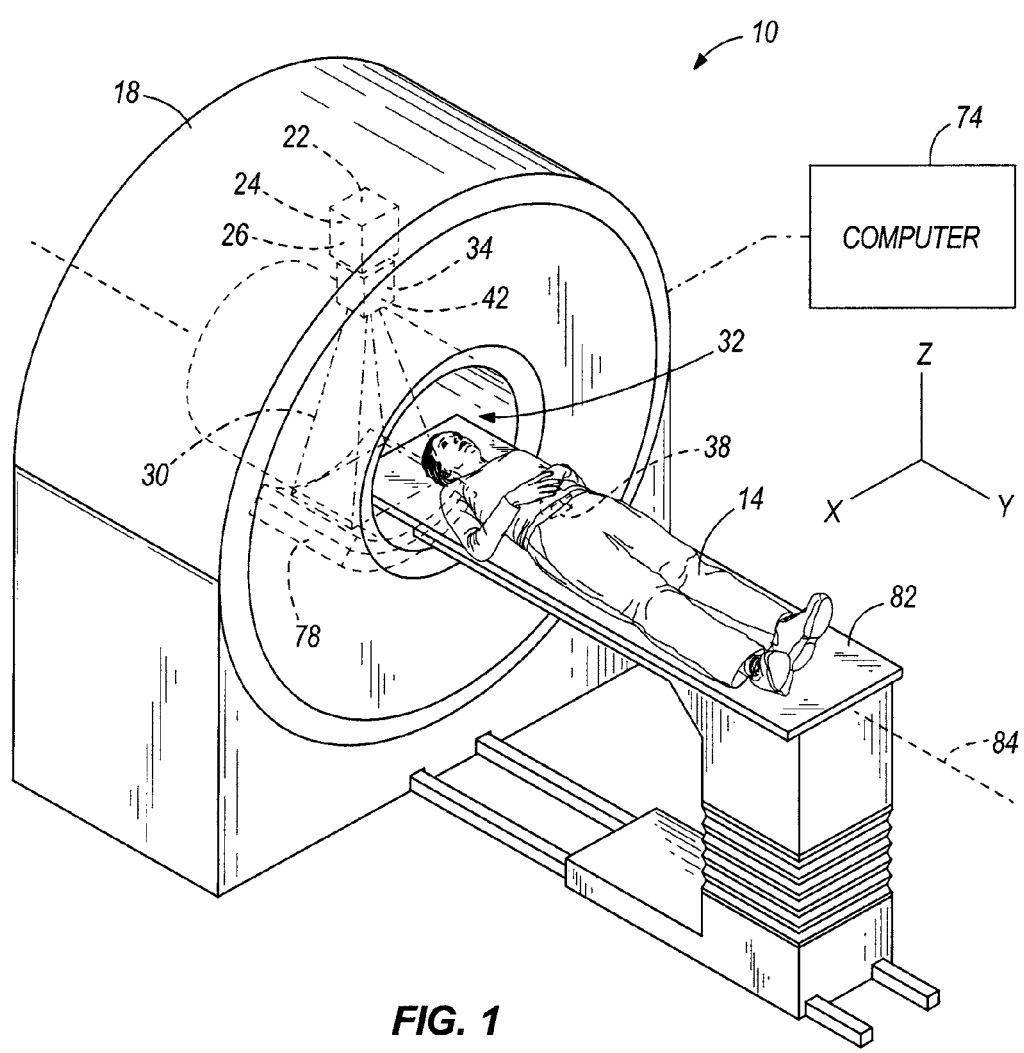
FIG. 1 is a perspective view of a radiation therapy treatment system.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein are meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

In addition, it should be understood that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium). As such, it should be noted that a plurality of hardware and software based devices, as well as a plurality of different structural components may be utilized to implement the invention. Furthermore, and as described in subsequent paragraphs, the specific mechanical configurations illustrated in the drawings are intended to exemplify embodiments of the invention and that other alternative mechanical configurations are possible.

FIG. 1 illustrates a radiation therapy treatment system 10 according to one embodiment of the invention that provides radiation therapy to a patient 14. The radiation therapy treatment can include photon-based radiation therapy, brachytherapy, electron beam therapy, proton, neutron, particle therapy, or other types of treatment therapy. The radiation therapy treatment system 10 includes a gantry 18. The gantry 18 supports a radiation module 22, which includes a radiation source 24 and a linear accelerator 26 (a.k.a. "a linac") that generates a beam 30 of radiation. Although the gantry 18 shown in FIG. 1 is a ring gantry (i.e., it extends through a full 360° arc to create a complete ring or circle), other types of mounting arrangements may also be employed. For example, a C-type, partial ring gantry, or robotic arm gantry arrangement could be used. Any other framework capable of positioning the radiation module 22 at various rotational and/or axial positions relative to the patient 14 may also be employed. In addition, the radiation source 24 may travel in path that does not follow the shape of the gantry 18. For example, the radiation source 24 may travel in a non-circular path even though the illustrated gantry 18 is generally circular-shaped. The gantry 18 of the illustrated embodiment defines a gantry aperture 32 into which the patient 14 moves during treatment.

The radiation module 22 also includes a modulation device 34 operable to modify or modulate the radiation beam 30. The modulation device 34 modulates the radiation beam 30 and directs the radiation beam 30 toward the patient 14. Specifically, the radiation beam 30 is directed toward a portion 38 of the patient 14. The portion 38 may include the patient's entire body, but is generally smaller than the patient's entire body and can be defined by a two-dimensional area and/or a three-dimensional volume. A portion may include one or more regions of interest. For example, a region desired to receive the radiation, which may be referred to as a target or target region, is an example of a region of interest. Another type of region of interest is a region at risk. If a portion includes a region at risk, the radiation beam is preferably diverted from the region at risk. The patient 14 may also have more than one target region that needs to receive radiation therapy. Such modulation is sometimes referred to as intensity modulated radiation therapy ("IMRT").

The portion 38 may include or be referred to as a target or target region or a region of risk. If the portion 38 includes a region at risk, the radiation beam 30 is preferably diverted from the region at risk. Such modulation is sometimes referred to as intensity modulated radiation therapy ("IMRT").

Figure 2:
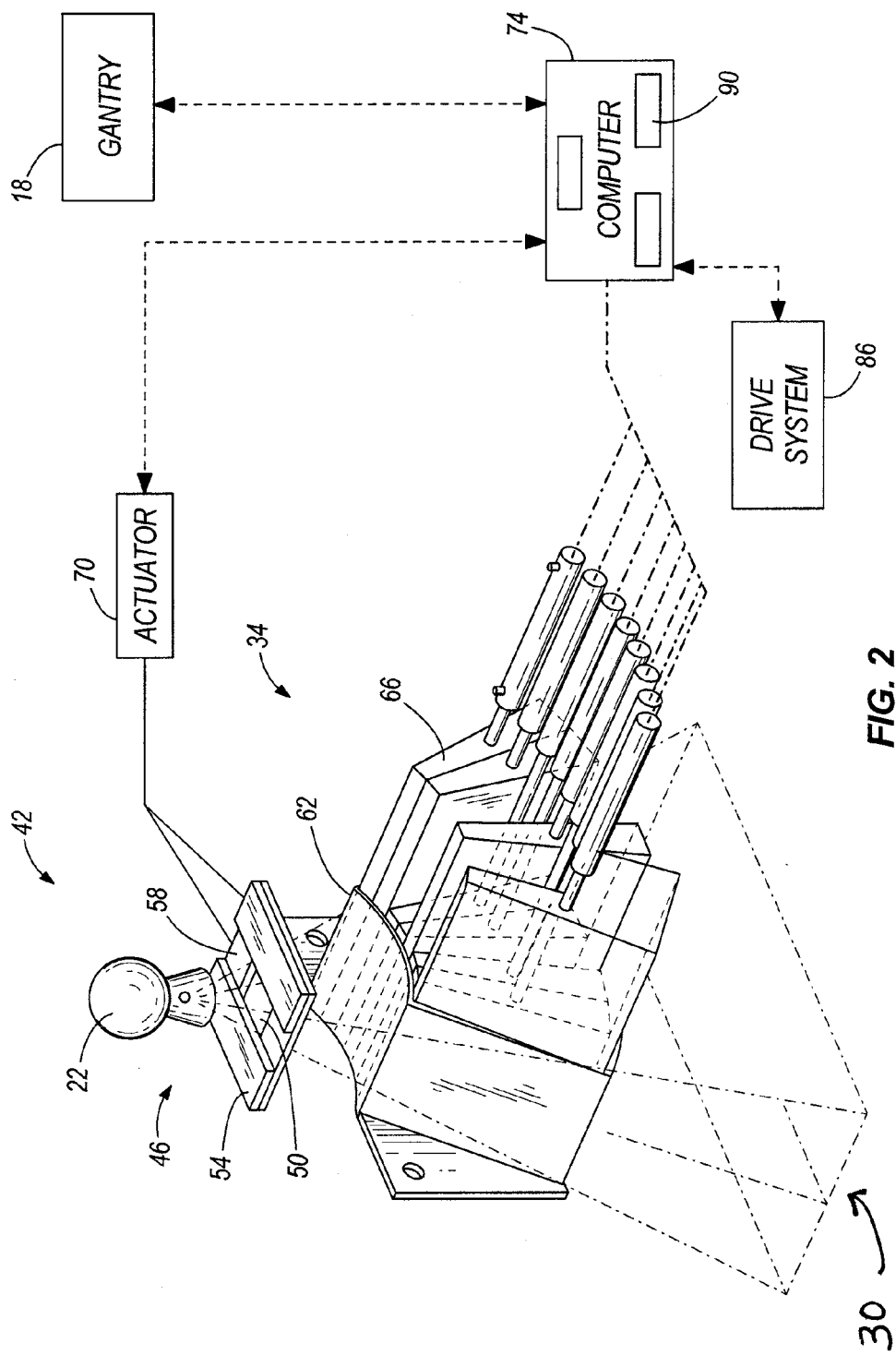
FIG. 2 is a perspective view of a multi-leaf collimator that can be used in the radiation therapy treatment system of FIG. 1.

The modulation device 34 includes a collimation device 42 as illustrated in FIG. 2. The collimation device 42 includes a set of jaws 46 that define and adjust the size of an aperture 50 through which the radiation beam 30 may pass. The jaws 46 include an upper jaw 54 and a lower jaw 58. The upper jaw 54 and the lower jaw 58 are moveable to adjust the size of the aperture 50. The position of the jaws 46 regulates the shape of the beam 30 that is delivered to the patient 14.

In one embodiment, as illustrated in FIG. 2, the modulation device 34 comprises a multi-leaf collimator 62 (a.k.a. "MLC"), which includes a plurality of interlaced leaves 66 operable to move between multiple positions to modulate the intensity of the radiation beam 30. It is also noted that the leaves 66 can be moved to a position anywhere between a minimally and maximally-open position. The plurality of interlaced leaves 66 modulate the strength, size, and shape of the radiation beam 30 before the radiation beam 30 reaches the portion 38 on the patient 14. Each of the leaves 66 is independently controlled by an actuator 70, such as a motor or an air valve, so that the leaf 66 can open and close quickly to permit or block the passage of radiation. The actuators 70 can be controlled by a computer or controller 74.

The radiation therapy treatment system 10 can also include a detector 78 (e.g., a kilovoltage or a megavoltage detector), as illustrated in FIG. 1, that receives the radiation beam 30. The linear accelerator 26 and the detector 78 can also operate as a computed tomography ("CT") system to generate CT images of the patient 14. The linear accelerator 26 emits the radiation beam 30 toward the portion 38 of the patient 14. The portion 38 absorbs some of the radiation. The detector 78 detects or measures the amount of radiation absorbed by the portion 38. The detector 78 collects the absorption data from different angles as the linear accelerator 26 rotates around and emits radiation toward the patient 14. The collected absorption data is transmitted to the computer 74, and the computer 74 processes the collected adsorption data to generate images of the patient's body tissues and organs. The images can also illustrate bone, soft tissues, and blood vessels.

The system 10 can also include a patient support device, shown as a couch 82 in FIG. 1, to support at least a part of the patient 14 during treatment. For example, while the illustrated couch 82 is designed to support the patient's entire body, in other embodiments of the invention, the patient support device can be designed to support only a part of the patient 14 during treatment. The couch 82, or at least portions thereof, moves into and out of the field of radiation along an axis 84. The couch 82 is also capable of moving along the X and Z axes as illustrated in FIG. 1.

Figure 3:
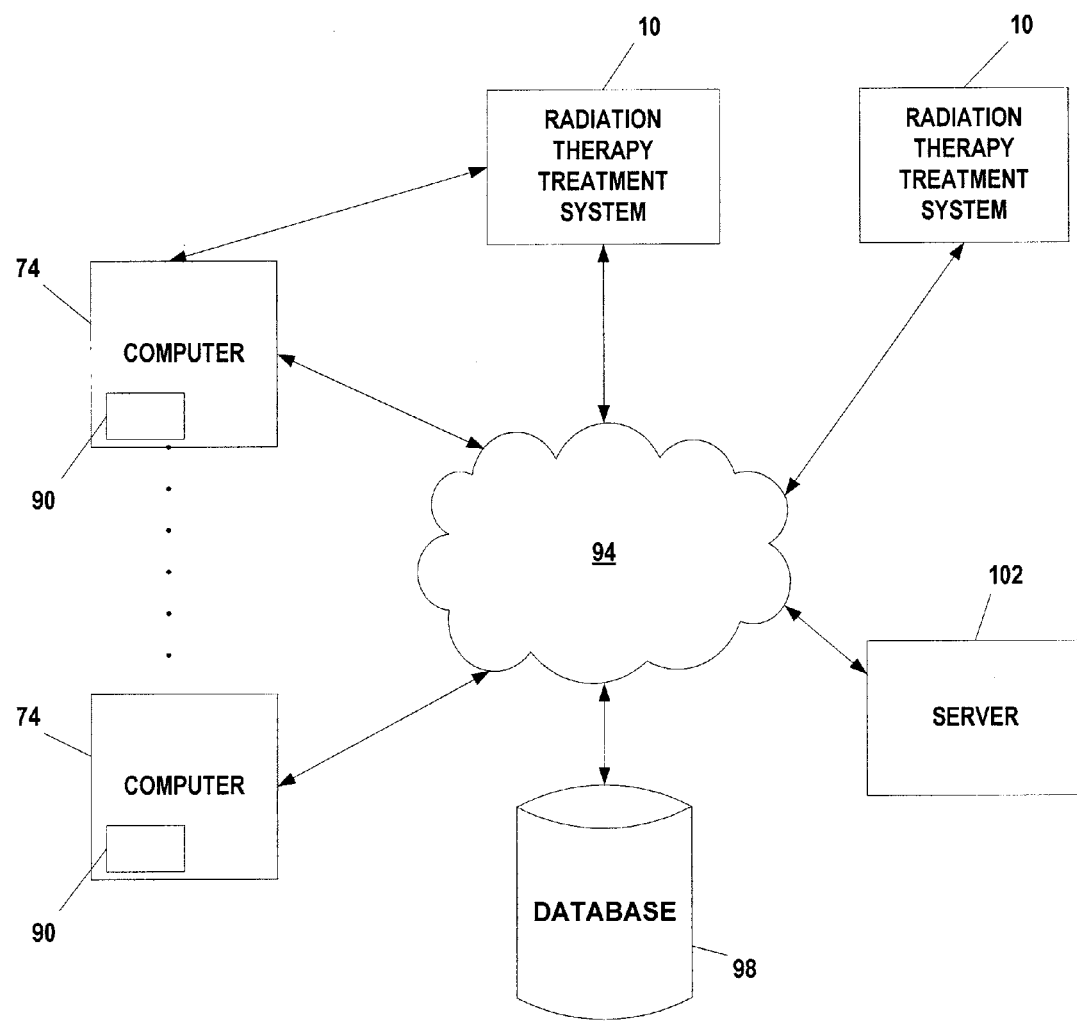
FIG. 3 is a schematic illustration of the radiation therapy system of FIG. 1.

The computer 74, illustrated in FIGS. 2 and 3, can include typical hardware such as a processor, I/O interfaces, and storage devices or memory (e.g., non-transitory computer-readable medium). The computer 74 also can include any suitable input/output device adapted to be accessed by medical personnel. The computer 74 can also include input devices such as a keyboard and a mouse. The computer 74 can further include standard output devices, such as a monitor. In addition, the computer 74 can include peripherals, such as a printer and a scanner. The computer 74 can also include typical software, such as an operating system for running various software programs and/or a communications application. In particular, the computer 74 can include a software program(s) 90 that operates to communicate with the radiation therapy treatment system 10.

As shown in FIG. 3, the computer 74 can be networked with one or more radiation therapy treatment systems 10 and other computers 74. The other computers 74 may include additional and/or different computer programs and software and are not required to be identical to the computer 74 described herein. In one embodiment, the computer 74 is networked with the radiation therapy treatment system 10 via one or more dedicated connections 92. In other embodiments, the computers 74 and radiation therapy treatment system 10 are networked via one or more networks 94. The computers 74 and radiation therapy treatment systems 10 can also communicate with a database(s) 98 and/or a server(s) 102 over the network 94. It is noted that all or portions of the software program(s) 90 included in the computer 74 could reside on the server(s) 102.

The network 94 can be built according to any networking technology or topology or combinations of technologies and topologies and can include multiple sub-networks. Connections between the computers 74 and systems 10 shown in FIG. 3 can be made through local area networks ("LANs"), wireless area networks ("WLANs"), wide area networks ("WANs"), public switched telephone networks ("PSTNs"), Intranets, the Internet, or any other suitable networks. In a hospital or medical care facility (collectively referred to as a health-care facility), communication between the computers 74 and systems 10 shown in FIG. 3 can be made through the Health Level Seven ("HL7") protocol with any version and/or other required protocol. HL7 is a standard protocol that specifies the implementation of interfaces between two computer applications (sender and receiver) from different vendors for electronic data exchange in health care environments. HL7 can allow health care institutions to exchange key sets of data from different application systems. Specifically, HL7 can define the data to be exchanged, the timing of the interchange, and the communication of errors to the application. The formats are generally generic in nature and can be configured to meet the needs of the applications involved.

Communication between the computers 74 and systems 10 illustrated in FIG. 3 can also occur through the Digital Imaging and Communications in Medicine ("DICOM") protocol with any version and/or other required protocol. DICOM is an international communications standard developed by the National Electrical Manufacturers Association ("NEMA") that defines the format used to transfer medical image-related data between different pieces of medical equipment. DICOM RT refers to the standards that are specific to radiation therapy data.

The two-way arrows in the drawings generally represent two-way communication and information transfer between the network 94 and any one of the computers 74, the radiation therapy treatment systems 10, and other components shown in FIG. 3. However, for some medical equipment, only one-way communication and information transfer may be necessary.

Figure 4:
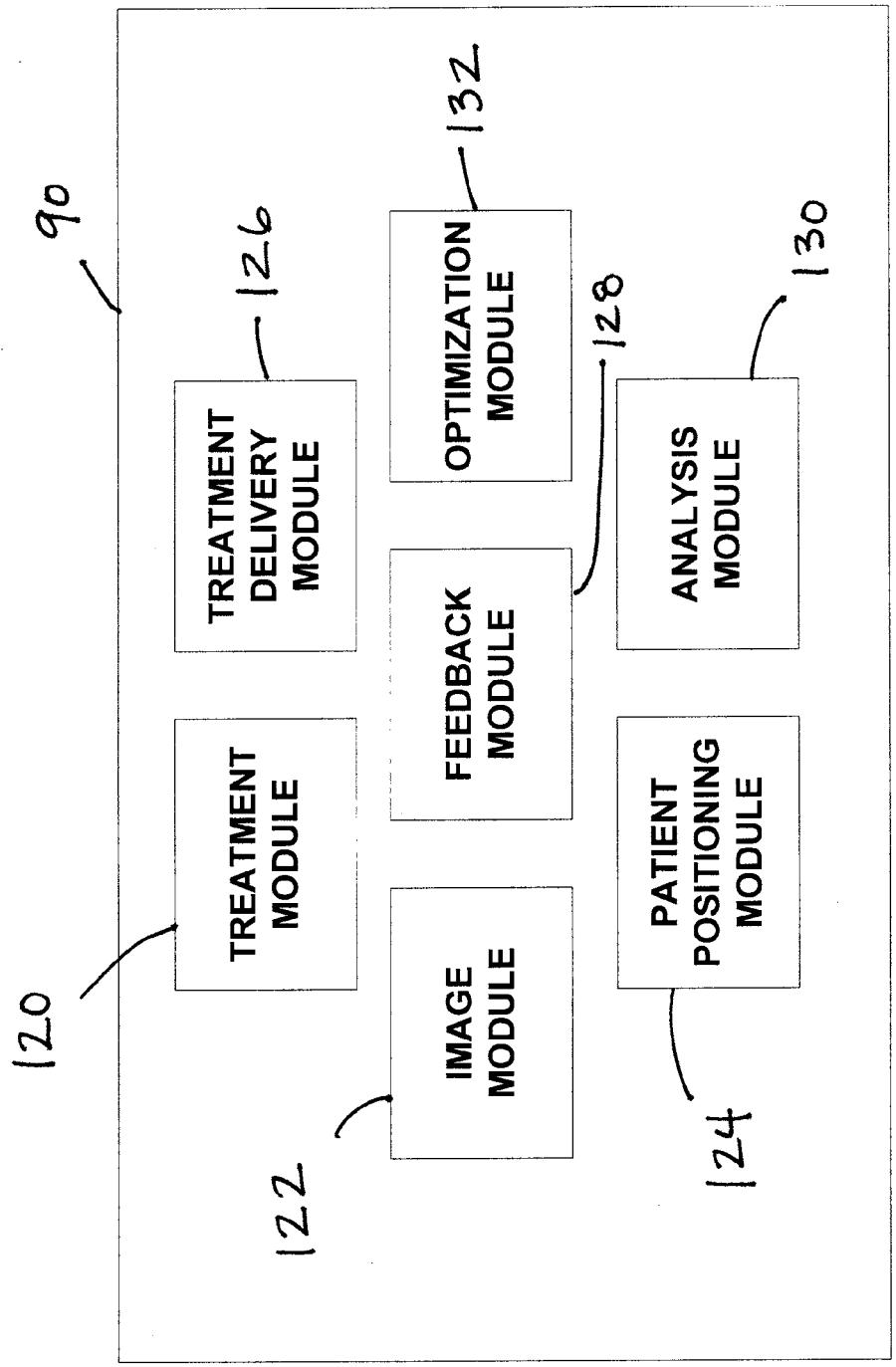
FIG. 4 is block diagram of a software program that can be used in the radiation therapy system of FIG. 1.

The software program 90 can include a plurality of modules that communicate with one another to perform functions of the radiation therapy treatment process. For example, as shown in FIG. 4, the modules can include a treatment plan module 120 operable to generate a treatment plan for the patient 14, an image module 122 operable to acquire images of at least a portion of the patient 14, a patient positioning module 124 operable to position and align the patient 14, a treatment delivery module 126 operable to instruct the radiation therapy treatment system 10 to deliver radiation to the patient 14 according to the treatment plan, a feedback module 128 operable to receive data from the radiation therapy treatment system 10 during and/or after a patient treatment, an analysis module 130 operable to analyze the data from the feedback module 122 or any of the other modules, and an optimization module 132 operable to optimize the treatment plan. Generally, optimization is a process in which the appropriate beam pattern, position, and intensity are calculated based on the physician's prescription for how much radiation the target should receive, as well as acceptable levels for surrounding structures. Functions and applications described below are performed by the optimization module 132. However, it should be understood that the functionality performed by each module can be distributed and combined among and between multiple modules.

Existing optimization modules and applications use a voxel-based beamlet-superposition ("VBS") framework that requires pre-calculation and storage of a large amount of beamlet data, which results in large temporal and spatial complexity. However, as described in more detail below, the optimization module 132 uses a non-voxel-based broad-beam ("NVBB") framework for performing IMRT optimization, which allows it to perform direct treatment parameter optimization ("DTPO"). In the NVBB framework, both the objective functional and the derivatives are evaluated based on a continuous viewpoint of a target volume. Therefore, the NVBB framework abandons "voxel" and "beamlet" representations used in the VBS framework. Thus, pre-calculation and storage of beamlets is no longer needed. As a consequence, the NVBB framework has linear complexities of ($O(N^3)$) in both space and time. Furthermore, when implemented on a graphics processing unit ("GPU"), the low-memory, full computation, and data parallel nature of the NVBB framework is even more efficient.

The NVBB framework can be incorporated with a treatment planning system ("TPS"), such as the Tomotherapy® TPS. The Tomotherapy® TPS using the NVBB framework can run on a single workstation with one GPU card (the "NVBB-GPU implementation"). As described in more detail below with respect to Table 8, extensive verification/validation tests were performed in house and via third parties. Benchmarks on dose accuracy, plan quality, and throughput were compared with a TPS based on the VBS framework using a computer cluster with 14 nodes (the "VBS-cluster implementation"). For all tests, the dose accuracy of the two TPS implementations were comparable (i.e., within 1%). In addition, plan qualities were comparable with no clinically significant difference for most cases except that superior target uniformity was seen in the NVBB-GPU implementation for some cases (see, e.g., FIG. 16). Furthermore, the planning time using the NVBB-GPU implementation was reduced many folds over the VBS-cluster implementation.

Therefore, the NVBB framework for IMRT optimization provides many advantages. For example, by taking a continuous viewpoint of a target volume, the flexibility of the objective functional formulation (described below) is increased, which provides derivative evaluations and enables direct optimization of various treatment parameters. This flexible model easily accounts for non-linear effects, such as tongue and grove ("T&G"), leakage, different leaf latencies, etc.

The NVBB framework also discards the beamlet model and does not require pre-calculation nor large memory storage. Without the voxel and beamlet representations, voxel size effect that contributes to dose calculation errors is also reduced. In addition, the NVBB framework implements dose and derivative calculation with linear spatial and temporal complexity. This reduces the problem size, lessens memory demand, and increases speed. This feature also enables dose calculation and IMRT optimization in a much finer grid, thus providing better spatial resolution than what is currently affordable. The full parallelization and low memory nature of the framework also enables the NVBB framework to be implemented in a GPU instead of a computer cluster. Thus, a single personal computer, even a laptop, can efficiently perform optimization. In addition, with the elimination of beamlet calculation, the addition of efficient dose and derivative calculation, and the use of a GPU, treatment planning time for the NVBB framework is reduced many folds compared with the conventional VBS framework running on a computer cluster even when the NVBB framework is run on a single workstation.

Furthermore, as described in more detail below, the NVBB framework adopts an "adaptive full dose correction" approach that combines the advantages of full dose (accuracy) and approximate dose (efficiency), which makes the "iteration dose" approach the full dose and the "optimization dose" approach the final dose with a high level of accuracy. Further still, the beam's eye view ("BEV") coordinate system and the associated NVBB ray-tracing provide efficient solutions for applications related to divergent beams, such as dose calculation, CT image reconstruction, etc.

Before the NVBB framework is disclosed in more detail, it should be noted that the following notations will be used throughout this document:

$\vec{p}$: treatment parameters to be optimized. $p_m$ is the mth parameter
u: two-dimensional point on the BEV plane u=(u,v)
x: three-dimensional point, x=(x,y,z) in Cartesian coordinates, x=(u,v,r) in BEV coordinates
D: three-dimensional dose distribution. D(x) is the dose at x.
$D_{\vec{p}}$ is the dose distribution dependent on parameters $\vec{p}$
$\tilde{D}$: approximate dose distribution
$\ddot{D}$: full (accurate) dose distribution D*: dose distribution in BEV coordinates, denoted with the superscript *
$\Im(D)$: objective functional that is a function of the dose distribution D
$F_D$: component of the objective function. $F_D$ is defined on the three-dimensional space
$G_D$: derivative of $F_D$ with respect to the spatial position $$G_D(x) = \frac{\partial F_D(x)}{\partial x}$$

f: fluence map defined on the BEV plane with f(u) denoting the fluence value at u
k: fluence convolution kernel defined on the BEV plane
g: convolution of f and k, i.e., g=f⊗k, defined on the BEV plane
$h_m$: derivative of f with respect to $p_m$, defined on the BEV plane, $$h_m = \frac{\partial f}{\partial p_m}$$

$e_m$: convolution of $h_m$ and k, $e_m$=$h_m$⊗k, defined on the BEV plane

In addition, for the reader's convenience, some abbreviations used in this document are listed below:

| | |
|---|---|
| BEV: | Beam's Eye View |
| PV-CS: | Patient Volume Coordinate System |
| VBS: | Voxel-based Beamlet-Superposition |
| NVBB: | Non-Voxel-based Broad-Beam |
| CCCS: | Collapsed-Cone Convolution/Superposition |
| FCBB: | Fluence-Convolution Broad-Beam |
| DTPO: | Direct Treatment Parameter Optimization |
| FMO: | Fluence Map Optimization |
| DAO: | Direct Aperture Optimization |
| GPU: | Graphics Processing Unit |
| TPS: | Treatment Planning System |
| LUT: | Look-Up Table |

As noted above, treatment planning for IMRT, including fixed-beam IMRT, volumetric modulated arc therapy ("VMAT"), and Tomotherapy® IMRT, involves a large scale (LS) or very large scale (VLS) optimization problem. The optimization problem can generally be categorized into two groups: fluence map optimization ("FMO") and direct aperture optimization ("DAO") (which is sometimes referenced to direct machine parameter optimization ("DMPO") when a gradient-based approach is used instead of a stimulated annealing method).

FMO is completed in two steps. The first step includes optimizing the fluence map to meet clinical objectives, and the second step includes making the fluence map deliverable through segmentation or leaf sequencing procedures. One advantage of FMO is that it includes simple mathematical formulation including derivatives, which makes it easy to implement. However, by decoupling FMO from treatment plan optimization, the MLC leaf-sequencing problem still must be solved, which causes a potential loss of treatment quality. In addition, the optimized fluence map is not always deliverable in a reasonable amount of time and a tradeoff has to be made between delivery time and conformity to the optimized fluence map.

DAO, on the contrary, makes an initial guess of deliverable apertures and optimizes the leaf position (aperture shape) directly. One advantage of DAO is that the optimized plan is generally always deliverable and usually results in fewer segments than FMO approaches. One disadvantage, however, is its complexity in mathematical formulation and solving. Therefore, heuristic approaches are generally applied to determine apertures, which results in longer computation time than FMO.

Both FMO and DAO approaches are based on the VBS framework described above. The VBS framework is based on two discrete representations: the voxel representation and beamlet (bixel, or pencil beam) representation. In this document, the terms "beamlet," "(finite size) pencil beam," "pixel," and "bixel" are treated as synonyms and each describe the result of geometrically dividing a broad beam into a finite number of finite-sized smaller beams. The term "broad beam" is generally the antonym of "beamlet." In a "broad beam" model, each projection of the radiation beam is regarded as a whole, without geometrical pixelization into finite-sized smaller beams.

In the VBS framework, the three-dimensional space is partitioned into (e.g., usually evenly spaced) volumetric pixels ("voxels") and the two-dimensional fluence map is partitioned into rectangular or hexagonal "bixels." The dose distribution of each bixel with unit intensity (a.k.a., beamlet) is pre-calculated and saved before optimization is performed. Therefore, in conventional IMRT optimization approaches based on the VBS framework, the voxel and beamlet representations are essential in formulating the objective functional (mainly for dose calculation) and derivative evaluations.

In particular, although the physical world is continuous, space is often discretized for computational purposes. For example, in conventional IMRT planning using the VBS framework, voxel and bixel discretizations are applied at the problem definition phase. The optimization problem is then defined as:

$$\min_{\vec{w}} \mathcal{J}(\vec{d}) \tag{1}$$

subject to $C_1(\vec{d})$ and $C_2(\vec{w})$ where $\vec{d}=B\vec{w}$. $\Im(.)$ is the objective functional defined over dose values $\vec{d}$ of certain voxels of interest. $\vec{d}$ is a vector of dose values of length N (number of voxels), and $\vec{w}$ is a vector of beamlet weights of length M (number of beamlets). The pre-calculated doses of each beamlet with unit intensity are organized into a matrix B with each column representing one beamlet and each row corresponding to one voxel. In conventional FMO or DAO approaches, dose at each voxel is a linear superposition of beamlet doses by different weights. Equation (1) holds for both FMO and DAO approaches with differences between FMO and DAO being present only in the constraint $C_2(\vec{w})$. For FMO approaches, the non-negativity constraint $\vec{w} \geq 0$ is sufficient. However, for DAO approaches, the constraints must include consecutiveness, inter-digitization, etc., which makes the DAO approach generally more complex than the FMO approach from a computational point of view.

The linear and discrete models in the VBS framework for IMRT optimization have the advantages of simplifying dose calculation and providing derivative evaluation in matrix form. For example, let $d_i$ denote the dose value at the ith voxel, $B_{i,j}$ the dose value of the jth beamlet at the ith voxel, and $w_j$ the weight of the jth beamlet. This yields:

$$d_i = \Sigma B_{i,j} w_j \tag{2}$$

Or in matrix form, $$\vec{d} = B\vec{w} \tag{3}$$

Similarly, the derivative of the dose vector with respect to the beamlet weight vector $\vec{w}$ is $\partial d_i/\partial w_j = B_{i,j}$, or in matrix form:

$$\frac{\partial \vec{d}}{\partial \vec{w}} = B \tag{4}$$

The derivative of the objective function with respect to beamlet weights can also be written in matrix form:

$$\frac{\partial \Im}{\partial \vec{w}} = B^t \cdot \frac{\partial \Im}{\partial \vec{d}} \tag{5}$$

Figure 5:
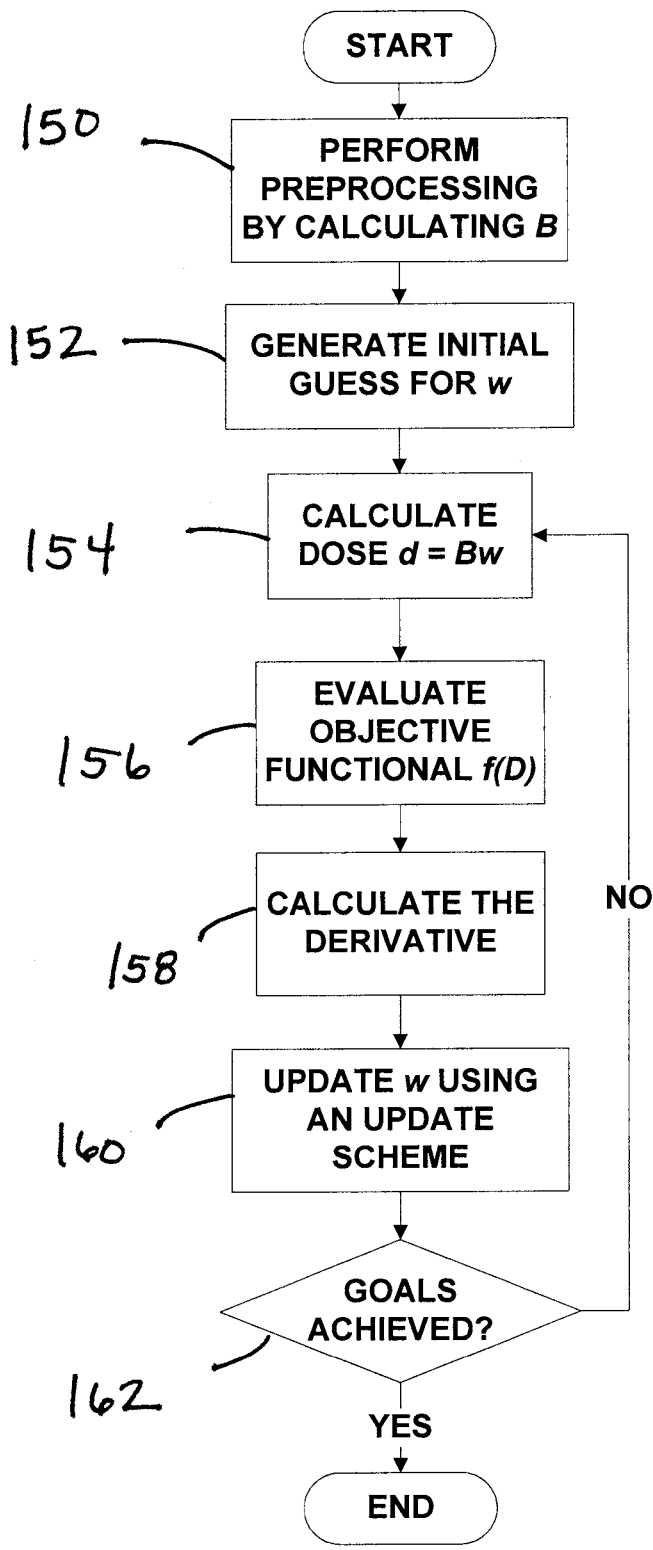
FIG. 5 is a flow chart schematically representing the iteration step for beamlet-based optimization.

Due to its mathematical simplicity in dose and derivative formulations, the conventional VBS framework is appealing and is used in virtually all TPSs. In general, iterative methods that involve both dose calculation (Equation (3)) and derivative calculation (Equation (5)) in each iteration are used to solve the optimization problem in Equation (1). FIG. 5 illustrates (e.g., in pseudo code) the VBS framework for IMRT optimization. As shown in FIG. 5, first preprocessing is performed, which includes calculating B (at 150). Next, an initial guess for $\vec{w}$ is generated (at 152). Then a dose is calculated using the equation $\vec{d}=B\vec{w}$ (at 154). Next, the objective function $\Im(\vec{d})$ is evaluated (at 156), and the derivative of the objective functional $$\frac{\partial \Im}{\partial \vec{w}} = B^t \cdot \frac{\partial \Im}{\partial \vec{d}}$$

is calculated (at 158). Next, $\vec{w}$ is updated using an update scheme (at 160). If the resulting $\vec{w}$ converges or satisfies clinical goals (at 162), the optimization is complete. Otherwise, the method is repeated starting with the dose calculation $\vec{d}=B\vec{w}$ (at 154).

As mentioned above, there are several drawbacks with using the VBS framework. First, the linear model $\vec{d}=B\vec{w}$ is only an approximation. Therefore, the VBS framework ignores many effects that are highly non-linear and hence hard to incorporate into the model, such as transmission, T&G leakage, different leaf latencies, etc. Consequently, the optimized dose deviates from what is actually delivered. There are some approaches that modify the linear model $\vec{d}=B\vec{w}$ to incorporate some of these effects, such as transmission. However, these modifications are very limited and lack flexibility.

The finite bixel resolution used in the VBS framework also limits the spatial resolution of the delivery system. Because of computation and storage limitations, the resolution of a beamlet is typically 5 to 10 millimeters. However, although the jaw and/or leaf of an MLC can move continuously to any position, the optimizer only instructs it to stay at discrete positions in accordance with the bixel resolution, which could significantly affect plan quality for some clinical cases when fine spatial resolution is in demand. The beamlet representation also lacks the flexibility for dynamic delivery. For example, because the beamlets in matrix B are pre-calculated, it is impossible to change the beam configuration (e.g. beam angle, jaw width, etc.) during optimization. This limitation also encumbers real-time optimization that accounts for patient motion and machine changes.

Furthermore, pre-calculation of thousands or even hundred of thousands of beamlets is very time consuming. Also, to make the iteration dose calculation $\vec{d}=B\vec{w}$ accurate enough for plan evaluation, the pre-calculated beamlet matrix B needs to be sufficiently accurate, which requires a significant amount of computation time. For example, a plan may take tens of minutes to hours to pre-calculate beamlets even with a 14-node computer cluster. The resulting beamlet matrix B is also huge. For example, in some systems, the number of voxels and the number of beamlets involved are on the order of 10 M and 100 K, respectively. Therefore, the matrix B, if saved in full, can be as large as 1 T (=10 M×100 K) in the number of elements, which requires computer memory that is too large to be handled by even a state-of-the-art workstation. It also takes a long time just to visit all voxels. Therefore, a distributed memory system, such as a computer cluster, and/or a heavy lossy compression/approximation of the beamlet matrix must be used to make the problem manageable. Currently, some systems use a computer cluster of 7 to 14 blades in addition to lossy compression of the beamlet matrix. The cluster solution, however, involves high capital and service cost demands, and the lossy compression/approximation may affect the dose accuracy and plan quality.

Calculation and validation of dose associated with a narrow beam (e.g., as small as approximately 5 millimeters) is also tricky due to a lack of electron equilibrium. Furthermore, there are conflicts between the bixel and voxel resolutions. Ideally, the bixel size should be as small as possible to approach the spatial resolution achievable by the MLC. On the other hand, the voxel size should be consistent with the CT resolution. However, to accurately calculate a beamlet dose, the voxel size needs to be much smaller than the bixel size. Otherwise dose calculation by ray-tracing through a small field is subject to large computation errors (sampling artifacts) because the voxel resolution is insufficient to capture the sharp transition of the dose. In practice, due to limitations of computer power, the voxel resolution (e.g., 2 to 5 millimeters) is comparable to the bixel resolution, which makes sampling artifacts unavoidable in the beamlet matrix B.

Therefore, as described in the previous paragraphs, the VBS framework for IMRT optimization has many problems, which significantly affect the plan quality and planning throughput. Moreover, recent development of general purpose GPUs with data-parallel stream processors enables an innovative approach of handling massive computation and makes high-performance computation affordable for general users. Compared with a central-processing-unit ("CPU") cluster, a single GPU card contains more processors (hundreds) but less memory, typically 1 gigabyte ("GB") or less. The enhanced computational power of GPUs make them suitable for computation-intensive applications, such as deformable registration, cone beam CT reconstruction, dose calculation, IMRT optimization, etc. However, because of its relatively small memory, a GPU is only suitable for applications with small data. Therefore, because the VBS framework is considered a very large scale (VLS) problem, it is difficult to implement in a GPU unless the underlying representations are fundamentally changed.

As previously noted, the NVBB framework does change the underlying representations used in IMRT optimization. Therefore, the NVBB framework is a low-memory framework for IMRT treatment planning. The NVBB framework replaces the VBS framework, which suffers from limited modeling powers, long pre-calculation time, and large spatial complexity, as described above. Rather than starting from voxel and bixel discretizations as in Equation (1), the NVBB framework starts with functional formulation of DTPO in a continuous format, which abandons voxel and beamlet representations. Based on this modification, both objective and derivative evaluations are in the continuous broad-beam framework, which eliminates beamlet pre-calculation and storage. Furthermore, using NVBB ray tracing makes dose calculation flexible and efficient. Also, the low memory, full computation, and data parallelization nature of the NVBB framework allows it to be efficiently implemented on a GPU, unlike conventional VBS frameworks.

Figure 6:
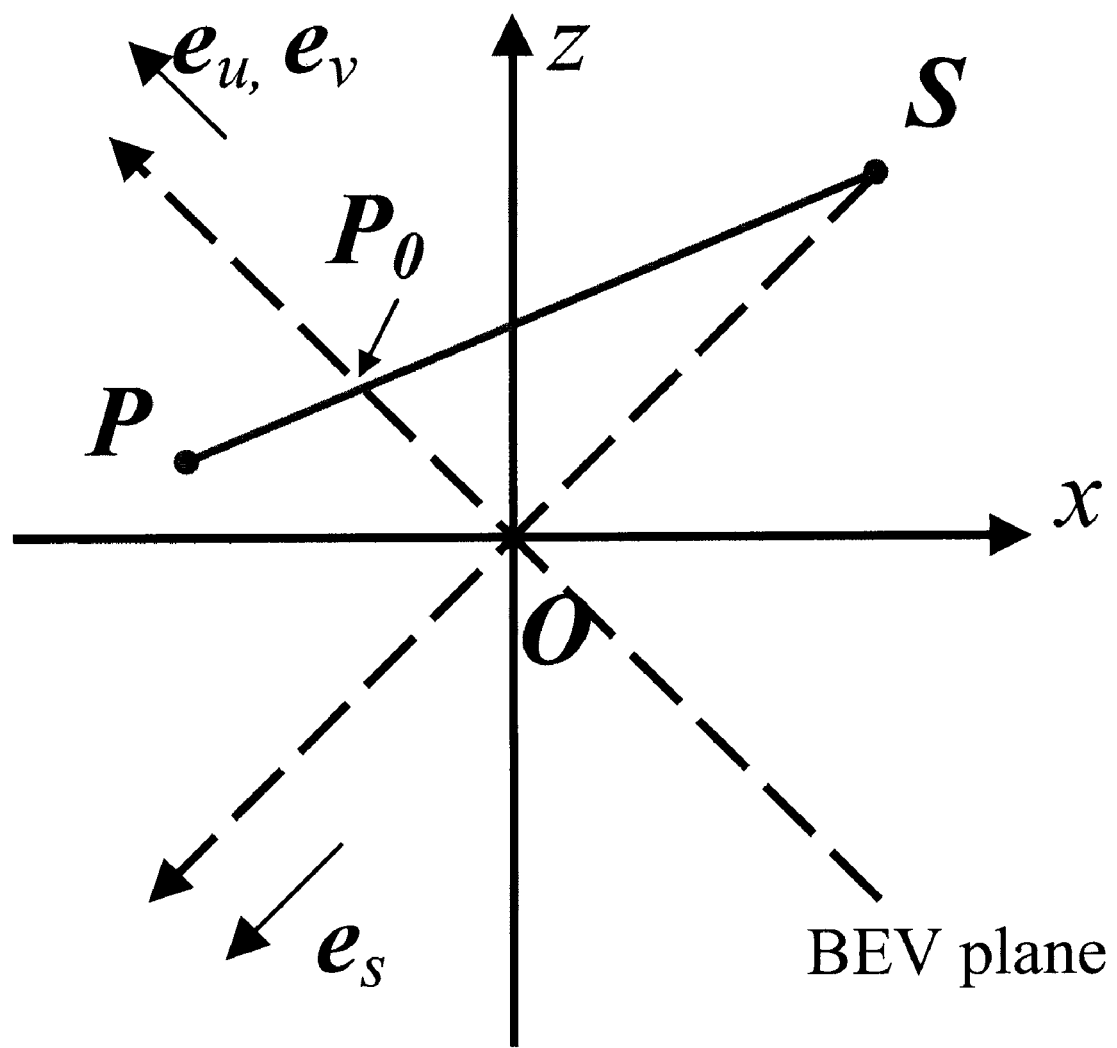
FIG. 6 illustrates a beam-eye-view coordinate system and Cartesian coordinate system.

The NVBB framework generally includes the following key techniques, which will each be described in more detail below.
1. The BEV coordinate system and NVBB ray-tracing
2. DTPO fluence map modeling
3. Adaptive full dose correction
4. FCBB method for approximate dose calculation
5. Efficient CCCS for full and final dose calculation
6. On the fly derivative calculation via accumulative NVBB ray tracing
7. Full GPU implementation BEV Coordinate System and NVBB Ray-Tracing In radiotherapy, three-dimensional volumes, such as density and dose, are usually defined in Cartesian coordinates, and so are the contour points and plan evaluation. A patient volume coordinate system ("PV-CS") can also be used, which is a Cartesian coordinate system ("Cartesian-CS") referenced to the patient. In PV-CS, assuming the patient is in the supine position, the positive X is from right to left, the positive Y is from posterior to anterior, and the positive Z is from superior to inferior. PV-CS is convenient for plan evaluation because it is in the patient's viewpoint. However, for applications that model machine delivery, it is convenient to adopt a machine viewpoint, such as the BEV coordinate system ("BEV-CS"). BEV-CS is useful in computation for point-source ray tracing. This is apparent because the geometry of BEV coincides with the physics modeling of the radiation beam path. Therefore, embodiments of the present invention alternate between the PV-CS and the BEV-CS. FIG. 6 illustrates the BEV-CS and the Cartesian-CS.

In radiotherapy, the point source S can revolve about the isocenter. For the sake of example only, assume the origin O of the PV-CS is at the isocenter. The source position in PV-CS can be written as $S=-se_s$, where $e_s$ is the unit vector from S to O and s is the source-to-axis distance ("SAD"). The BEV plane is defined as the plane that passes through O and is orthogonal to $e_s$. Two unit vectors $e_u$ and $e_v$ on the BEV plane are chosen so that $\{e_u, e_v, e_s\}$ form the basis of a right hand coordinate system. The BEV coordinates consist of Cartesian components from the BEV plane and a radial component, which is the distance from the source S. More precisely, for any point P, let $P_0=ue_u+ve_v$ denote the intersection of SP and the BEV plane. Then the BEV coordinate of P is (u,v,r), where $r=\|P-S\|$.

i. Transformation Between BEV and Cartesian Coordinates

BEV coordinates can be transformed into Cartesian coordinates and vice versa. For example, given the BEV coordinates (u,v,r) of P, then, in PV-CS, P can be written as:

$$P = ue_u + ve_v + (r - r_0)e_r, \quad (6)$$

where $$r_0 = \sqrt{s^2 + u^2 + v^2} \text{ and } e_r = \frac{se_s + ue_u + ve_v}{r_0} \quad (7)$$

Note that $r_0$ is the distance from the source to $P_0$, which is on the BEV plane. Conversely, given any point P in PV-CS, its BEV coordinates (u,v,r) can be obtained by:

$$r = \|P - S\|, \ u = P_0 \cdot e_u \text{ and } v = P_0 \cdot e_v \quad (8)$$

where $$P_0 = S - \frac{s^2}{(P-S) \cdot S}(P - S) \quad (9)$$

Equations (6) and (7) give the conversion from BEV coordinates to Cartesian coordinates, and Equations (8) and (9) give the conversion from Cartesian coordinates to BEV coordinates. There are no trigonometric functions involved in the transformations between BEV and Cartesian coordinates. Therefore, such transformations can be efficiently implemented in computer programs.

ii. Differential Volume for Infinitesimal Divergent Beam

Figure 7:
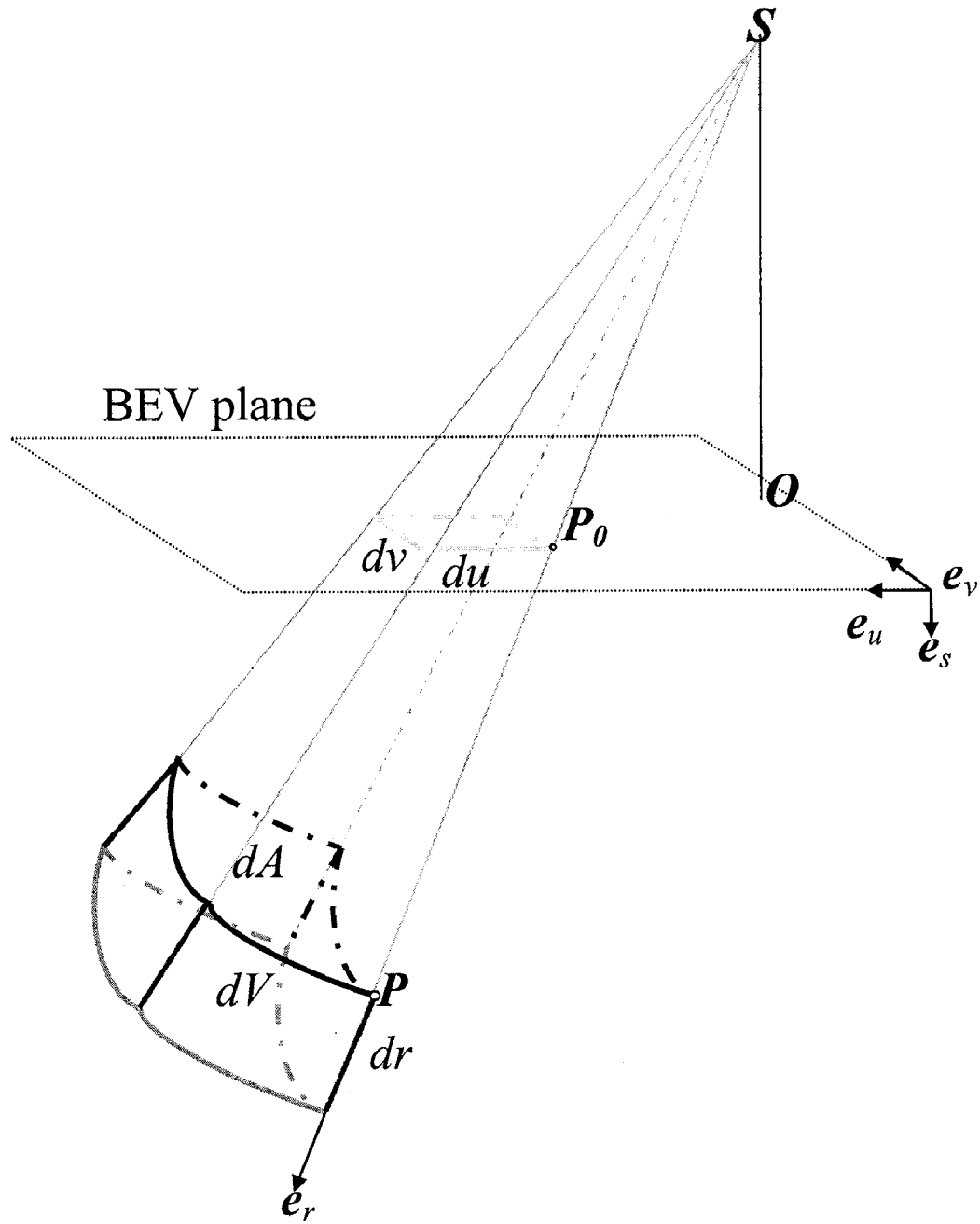
FIG. 7 illustrates a differential divergent beam in the beam-eye-view coordinate system.

The differential volume for an infinitesimal divergent beam in the BEV-CS is used to connect the continuous space with the discrete implementation and for describing NVBB ray tracing. FIG. 7 illustrates a differential divergent beam in the BEV-CS. Consider a differential divergent beam, illustrated in FIG. 7 as a cone, subtended by du×dv at vertex S. The beam intersects the reference plane at point $P_0$ with BEV coordinates (u,v,$r_0$). The corresponding differential solid angle is defined as the projected area of du×dv on the unit sphere:

$$d\Omega = \frac{s}{r_0^3} du dv \quad (10)$$

Thus, the area of the spherical cap of the differential cone at radius r is:

$$dA = r^2 d\Omega = \frac{r^2 s}{r_0^3} du dv \quad (11)$$

And the differential volume can be written as:

$$dV = dA dr = \frac{r^2 s}{r_0^3} du dv dr \quad (12)$$

Furthermore, defining:

$$a(r) = \frac{r_0^3}{r^2 s} \quad (13)$$

Then, the following equation can be used:

$$dV = \frac{1}{a(r)} du dv dr \quad (14)$$

Note that J(u,v,r)=1/a(r) is the Jacobian from BEV-CS to Cartesian-CS. For an algebraic derivation of the Jacobian J(u,v,r), see Appendix A. Also, note that a(r) and the Jacobian J(u,v,r) are used in NVBB ray tracing for dose calculation, derivative calculation, and inverse square correction in fluence transportation.

Direct Treatment Parameter Optimization

As noted above, the NVBB framework also uses DTPO fluence map modeling. Again, as previously described, instead of partitioning three-dimensional space into voxels and two-dimensional fluence maps into bixels, the NVBB framework adopts the continuous viewpoint and functional formulation. Using this representation, the DTPO performed by the NVBB framework can be generally described in continuous space as:

$$\min_{\vec{p}} \Im(D) \text{ subject to } C_1(D) \text{ and } C_2(\vec{p}) \quad (15)$$

where $\Im$ is the objective functional, and D is a dose distribution defined on the patient volume in $R^3$ and is a function of $\vec{p}$, which is a vector of treatment parameters to be optimized. $C_1(D)$ are patient dose constraints (e.g. minimal or maximal dose constraints, dose-volume histogram ("DVH") constraints, etc) and $C_2(\vec{p})$ are parameter constraints (e.g. non-negative leaf open time constraints, leaf position and velocity constraints, etc). The objective functional $\Im$ is a dose-based functional, which may include biological objectives that can be expressed as functionals of dose distributions. Note that the term "treatment parameters" used here has a broader sense than what is usually meant by the term "machine parameters." For example, treatment parameters refer to gantry speed, couch speed, projection angles, jaw angles, leaf open time, etc. Machine parameters, however, generally refers only to MLC apertures.

In general, the objective functional can be expressed as the integration of contribution from the whole space $R^3$:

$$\Im(D) = \iiint F_D(x) dx \quad (16)$$

where F is another functional of D and the integration is over the three-dimensional volume. For example, a commonly used objective functional is:

$$F_D(x) = A(x) \cdot (D(x) - P(x))^2$$

where A(x) is a position-dependent weight and P(x) is the desired dose at x. P is usually the prescription dose on the tumor and zero elsewhere.

In general, like other optimization problems, an iterative scheme is used in IMRT optimization. In each iteration, both the objective functional $\Im(D)$ and its derivative $\partial\Im/\partial p_m$ are evaluated, including verification of the constraints $C_1(D)$ and $C_2(\vec{p})$. For simplicity, the constraint part will be omitted hereinafter.

There are numerical methods that solve the optimization problem in Equation (15). Some methods require only objective functional evaluation, such as the down hill simplex, direction set, and simulated annealing method. Other methods require additional calculation of derivatives (gradient) of the objective functional, such as the conjugate gradient method, the Newton and quasi-Newton method, and the Levenberg-Marquardt method. Algorithms using derivatives (gradient-based) are usually much more efficient than those with function evaluation only. In this document, gradient-based optimization schemes are focused on. However, in general, regardless of what search method is used, evaluations of the objective functional and its derivatives are still important parts of optimization. Therefore, if function evaluation and partial derivatives can be provided by a particular method, then optimization can be regarded as a black box algorithm. Many open-source or commercial software can also be used to solve Equation (15).

Figure 8:
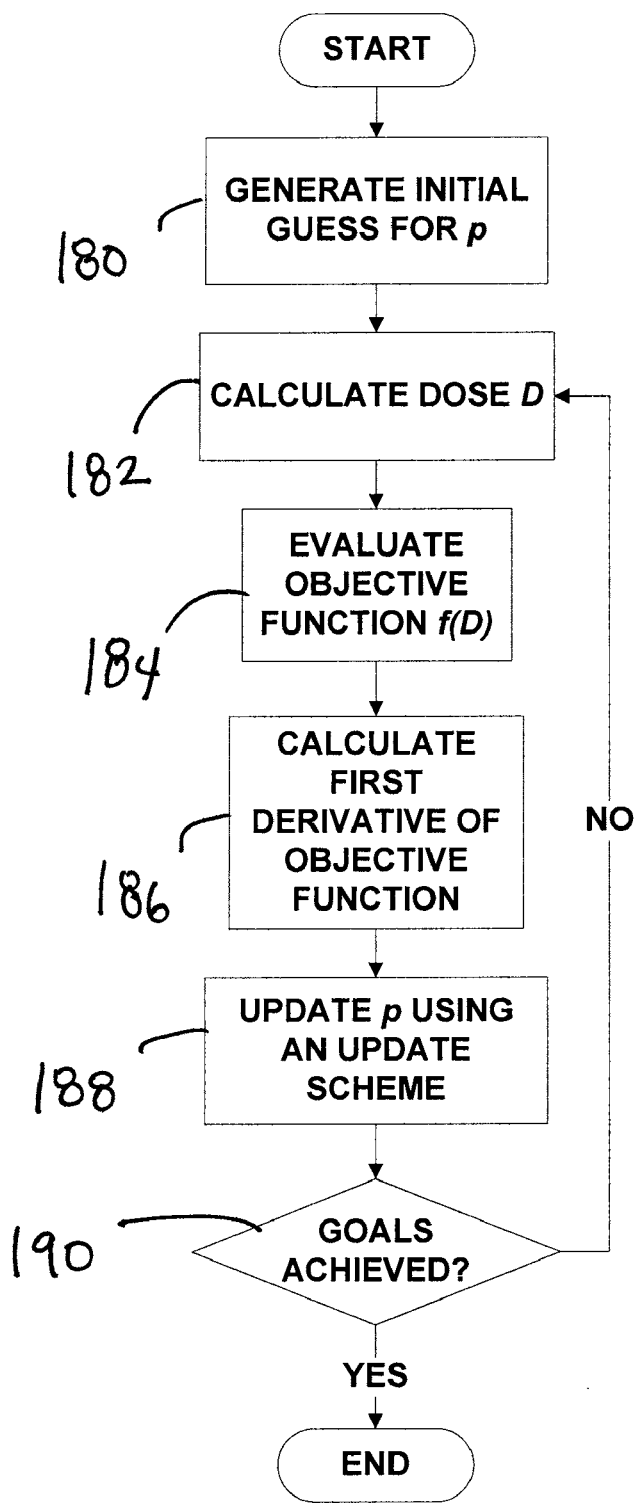
FIG. 8 is a flow chart schematically representing the iteration step for non-beamlet-based optimization.

A typical workflow for the gradient-based optimization scheme for the DTPO problem of Equation (15) is illustrated in FIG. 8 (e.g., in pseudo code). As shown in FIG. 8, first an initial guess for $\vec{p}$ is generated (at 180). Then a dose is calculated using the equation $D=D_{\vec{p}}(x)$ (at 182). Next, the objective functional $\Im(D)$ is evaluated (at 184), and the first derivative of the objective functional $$\frac{\partial \Im}{\partial \vec{p}}$$

is calculated (at 186). Next, $\vec{p}$ is updated using an update scheme (at 188). If the resulting $\vec{p}$ converges or satisfies clinical goals (at 190), the optimization is complete. Otherwise, the method is repeated starting with the dose calculation $D=D_{\vec{p}}(x)$ (at 182). Note that, in each iteration, dose is calculated (at 182) and partial derivatives are generated (at 186) to update the treatment parameters.

As illustrated in FIG. 8, because no voxel or beamlet representations are needed, no preprocessing is needed to generate the matrix B, as was needed in the VBS framework optimization illustrated in FIG. 5. Therefore, this computational process is eliminated as is the large storage requirement associated with the matrix B. However, without pre-calculation of the beamlet matrix B, both dose calculation and derivative calculation could be very time-consuming to achieve the desired accuracy if the brute force method is used. The NVBB framework solves this problem in three steps. First, the NVBB framework models contributions of treatment parameters and physical constraints in the continuously defined fluence map and calculates the derivatives of the fluence map with respect to changes of treatment parameters. Second, NVBB ray tracing is used to transform the two-dimensional fluence to three-dimensional dose and to calculate the derivative of the three-dimensional dose with respect to the two-dimensional fluence. Third, the chain rule is then applied to calculate the derivative of the objective functional with respect to the treatment parameters by combining the first and second steps. These three steps are described in more detail below. In particular, first fluence map modeling with respect to treatment parameters is described (e.g., using an example). Next, dose calculation and derivative calculation is described.

Fluence Map Modeling

The fluence map is an important component in IMRT dose calculation and optimization, and, therefore, it needs to be accurately modeled. In general, does calculation is modeled as steps:

$$\vec{p} \xrightarrow{1} f \xrightarrow{2} D \qquad (17)$$

The first step calculates the two-dimensional fluence map $f=f(u,v)$ based on the treatment parameters $\vec{p}$. The second step then uses the fluence map to calculate the three-dimensional dose. Note that only the does of one projection angle is considered. For multiple projections, the dose from each projection is added up.

The fluence map is usually defined on a reference plane that is perpendicular to the central axis of the radiation beam (i.e., the BEV plane). If the Monte Carlo dose calculation method is used, then the fluence map is replaced by the phase space defined on the entrance plane.

The first step, where accurate machine modeling, such as the penumbra, T&G effect and leakage are taken into account, is highly nonlinear. Fortunately, it involves only a two-dimensional fluence map f, and, thus, it has a computational demand that is lower than the second step that involves a three-dimensional volume. The second step, from the two-dimensional fluence map f to the three-dimensional dose distribution D, is linear but is more time-consuming. In particular, its linearity can be expressed as:

$$D_{af_1+bf_2}=aD_{f_1}+bD_{f_2} \qquad (18)$$

In principle, for DTPO, $f=f_{\vec{p}}$ and $\partial f/\partial \vec{p}$ need to be calculated for any treatment parameter to be optimized. For example, in dynamic jaw modeling, the treatment parameters to be optimized are the positions of left and right jaws. Similarly, in binary MLC modeling, the treatment parameters to be optimized are individual leaf open time. Other physical properties, such as cone effects, leakage, and T&G can also be included in the modeling as well. A description of two-dimensional MLC modeling, which consists of individual leaf pairs that can be modeled like dynamic jaws, is provided below.

i. Dynamic Jaw Modeling

In dynamic jaw modeling, the fluence map and its derivatives are described with respect to the jaw positions. Therefore, the question is, for a fixed projection, how does the jaw position affect the fluence map f. Because jaws move in one dimension and fluence can be approximately regarded as a one-dimensional function of jaw positions with both the jaw and fluence defined on the same axis, the problem is essentially a one-dimensional problem. For example, consider a fixed projection. Let l and r denote the left and right jaw positions, respectively. More explicitly, if jaw moves are in the "v" direction on the BEV plane, then the one-dimensional fluence map $f_{jaw}$ can be written as:

$$f_{jaw}(v)=O(l,r)C(v)\cdot(L(l,v)+R(r,v)-1) \qquad (19)$$

where C(v) is the cone shape (for the non-flattening-filtered field), O(l,r) is a jaw position dependant output factor, and L(l,v) and R(r,v) are the jaw profiles of the left and right jaws at position l and r, respectively. Assuming that the jaw profile L(l,v)(R(r,v)) can be approximated by the shift of $L_{l_0}(v)(R_{r_0}(v))$, respectively), which is one of the commissioned profiles, then Equation (19) can be approximated by:

$$f_{jaw}(v) \approx O(l,r) \cdot C(v) \cdot (L_{l_0}(v-(l-l_0)) + R_{r_0}(v-(r-r_0)) - 1) \tag{20}$$

Based on Equation (20), the derivatives can be written as:

$$\frac{\partial f_{jaw}}{\partial l}(v) = -\frac{\partial O}{\partial l}(l,r) C(v) \cdot \left(\frac{dL_{l_0}}{dv}\right)(v-(l-l_0)) \tag{21}$$

and $$\frac{\partial f_{jaw}}{\partial r}(v) = -\frac{\partial O}{\partial r}(l,r) \cdot C(v) \cdot \left(\frac{dR_{r_0}}{dv}\right)(v-(r-r_0)) \tag{22}$$

ii. Binary MLC Modeling

IMRT that uses a binary MLC (such as axial and helical radiation therapy) is different from IMRT that uses a two-dimensional MLC. Specifically, such a IMRT should model intra-leaf leakage (i.e., leakage through a leaf itself), interleaf leakage (i.e., T&G, leakage through leaf edge), and penumbra of the open field. In addition, the treatment parameters are individual leaf open times $\{t_j\}$.

Also, for this portion of the document, let the following symbols be defined as indicated:

$t_j$: open time of leaf j, $\{t_j\}$ denotes a leaf pattern which is one row of the sinogram.

T: time of one projection $\phi_j(u)$: fluence profile when leaf j is open and all others are closed $\Phi_{j-1,j}(u)$: fluence profile when both leaf j−1 and j are open and all others are closed $\phi_b$: intra-leaf background leakage profile (all leaves closed, baseline)

Note that $\{t_j\}$ and T are treatment planning parameters while the other parameters are from machine commissioning data.

Furthermore, let $\varphi_i$ denote the discrepancy between simultaneous and individual opening of leaf i and i−1 with baseline removed:

$$\varphi_i = \Phi_{i-1,i} - \phi_b - (\phi_{i-1} - \phi_b + \phi_i - \phi_b) \tag{23}$$

$$= \Phi_{i-1,i} - (\phi_{i-1} + \phi_i) + \phi_b$$

Then, the fluence profile of a given leaf pattern $\{t_j\}$ is:

$$f_{leaf}(u) = T\phi_b(u) + \sum_{j=1}^{J} t_j(\phi_j(u) - \phi_b(u)) + \sum_{j=1}^{J} \min(t_{j-1}, t_j)\varphi_j(u) \tag{24}$$

where J is the total number of leaves. The first term is the background radiation when all leaves are closed. The second term is the increase of radiation caused by opening each leaf according to the leaf pattern $\{t_j\}$. The third term is the correction for the discrepancy of simultaneous and individual opening of adjacent leaves caused by interleaf leakage and the T&G effect.

For the gradient-based optimization, the derivative of $f_{leaf}$ with respect to $t_j$ also needs to be calculated:

$$\frac{\partial f_{leaf}}{\partial t_j} = \phi_j - \phi_b + H(t_{j-1} - t_j)\varphi_j \tag{25}$$

where H is the step function $$H(t) = \begin{cases} 1, & t \geq 0 \\ 0, & t < 0 \end{cases} \tag{26}$$

By combining the jaw and leaf modeling, for any given projection, the two-dimensional fluence map for a radiation treatment delivery with dynamic jaw and leaf motion is provided:

$$f = f_{l,r,\{t_j\}}(u,v) = f_{jaw}(v) \cdot f_{leaf}(u) \tag{27}$$

And the derivatives with respect to the treatment parameters $l, r, \{t_j\}$ can be calculated using Equations (21), (22) and (24).

$$\frac{\partial f}{\partial l} = \frac{\partial f_{jaw}}{\partial l} f_{leaf} \tag{28}$$

$$\frac{\partial f}{\partial r} = \frac{\partial f_{jaw}}{\partial r} f_{leaf} \tag{29}$$

$$\frac{\partial f}{\partial t_j} = f_{jaw} \frac{\partial f_{leaf}}{\partial t_j} \tag{30}$$

iii. Two-Dimensional MLC Modeling

For the case of two-dimensional MLC, if only one leaf pair is focused on, then the problem is effectively a one-dimensional problem and can be similarly modeled like dynamic jaw motion. Therefore, Equations (20) to (22) are sufficient to describe one-dimensional fluence map modeling. However, unlike the dynamic jaw modeling, two-dimensional MLC needs special attention on the leaf edge and T&G modeling. Detailed descriptions of two-dimensional MLC modeling can be found in: Bortfeld T., Kahler D., Waldron T., and Boyer A., *X-ray Field Compensation with Multileaf Collimators*, INT'L J. RADIATION, ONCOLOGY, BIOLOGY, & PHYSICS, 1994, at 28, 723-30; Deng J., Pawlicki T., Chen Y., Li J., Jiang S. B., and Ma C. M., *The MLC Tongue-and-Groove Effect on IMRT Dose Distributions*, PHYSICS IN MED. & BIOLOGY, 2001, at 46, 1039-60; Lorenz F., Killoran J., Wenz F, and Zygmanski P., *An Independent Dose Calculation Algorithm for MLC-Based Stereotactic Radiotherapy*, MED. PHYSICS, 2007, at 34, 1605-14; and Lorenz F., Nalichowski A., Rosca F., Killoran J., Wenz F. and Zygmanski P., *An Independent Dose Calculation Algorithm for MLC-Based Radiotherapy Including the Spatial Dependence of MLC Transmission*, PHYSICS MED. BIOLOGY, 2008, at 53, 557.

Dose Calculation

A dose engine is an important part of any TPS. The dose engine generally consists of two components: machine modeling and dose calculation. Machine modeling is a patient-independent commissioning procedure, and the dose calculation component is the component that is actively utilized during treatment planning. In fact, for IMRT, physicists and physicians rely heavily on dose calculation to define plans. There are typically two places where dose calculation is needed. First, during IMRT optimization, the dose is calculated whenever the plan is updated, which is used as the driving force for the next iteration to reach a desirable plan. After a plan is optimized, the dose is re-calculated with all machine constraints modeled for final plan evaluation and for comparison with the measurement. The dose calculated during plan optimization is called the "iteration dose," the dose from the last optimization iteration is called the "optimization dose," and the dose for final evaluation is called the "final dose." Ideally, the optimization dose should match the final dose and the final dose should match the measurement.

IMRT optimization involves hundreds of iterations to reach a plan. A new three-dimensional dose volume needs to be calculated whenever the plan is updated (e.g., usually during each iteration). Therefore, on one hand, dose calculation must be fast enough to finish hundreds of iterations in a reasonable amount of time. However, on the other hand, the calculated dose must be accurate enough to make plan evaluation meaningful. Accordingly, there are tradeoffs between accuracy and computation time among various dose calculation algorithms. For example, the Monte Carlo ("MC") and full convolution/superposition ("C/S") methods are regarded as accurate, but they are very time-consuming. Similarly, some approximate dose engines, such as the finite size pencil beam ("FSPB"), are much faster than MC and C/S but have limited accuracy, especially when there are significant heterogeneities. Accurate but slow dose calculation is often called "full dose calculation," and less accurate but faster dose calculation is often called "approximate dose calculation."

Full dose calculation may take minutes to hours of CPU time for a complex IMRT plan. Therefore, full dose calculation is often not affordable for every iteration and an alternative scheme may be employed to reduce calculation time without sacrificing too much of accuracy.

A tradeoff between speed and accuracy is undertaken to some extent in the VBS framework via pre-calculation of the beamlet matrix B, an off-line process that utilizes a slow full dose engine. During the optimization iteration, dose is calculated as a simple matrix product $D=B\vec{w}$. However, there are drawbacks in the VBs framework as discussed in the previous section. Therefore, embodiments of the present invention use an "adaptive full dose correction" scheme that combines advantages of the approximate dose engine (e.g., speed) and the full dose engine (e.g., accuracy).

Adaptive Full Dose Correction

To take advantage of the accuracy of full dose calculation (e.g. MC or CCCS methods) and the efficiency of approximate dose calculation (e.g. FSPB methods), hybrid methods are proposed by various investigators. The NVBB framework adopts the "additive correction matrix" method proposed by Siebers et al. (see, e.g., Siebers J. V., Lauterbach M., Tong S., Wu Q. and Mohan R., *Reducing Dose Calculation Time for Accurate Iterative IMRT Planning*, MED. PHYSICS, 2002, at 29, 231-237, the entire contents of which are incorporated herein by reference).

For example, let $\ddot{D}$ denote the full dose, $\tilde{D}$ the approximate dose, and $\Delta D_{f_0}$ their difference associated with the fluence map $f_0$.

$$\Delta D_{f_0} = \ddot{D}_{f_0} - \tilde{D}_{f_0} \quad (31)$$

For the fluence map f that is close to $f_0$, a correction-based dose $D_f$ can then be defined:

$$D_f = \tilde{D}_f + \Delta D_{f_0} \quad (32)$$

Figure 9:
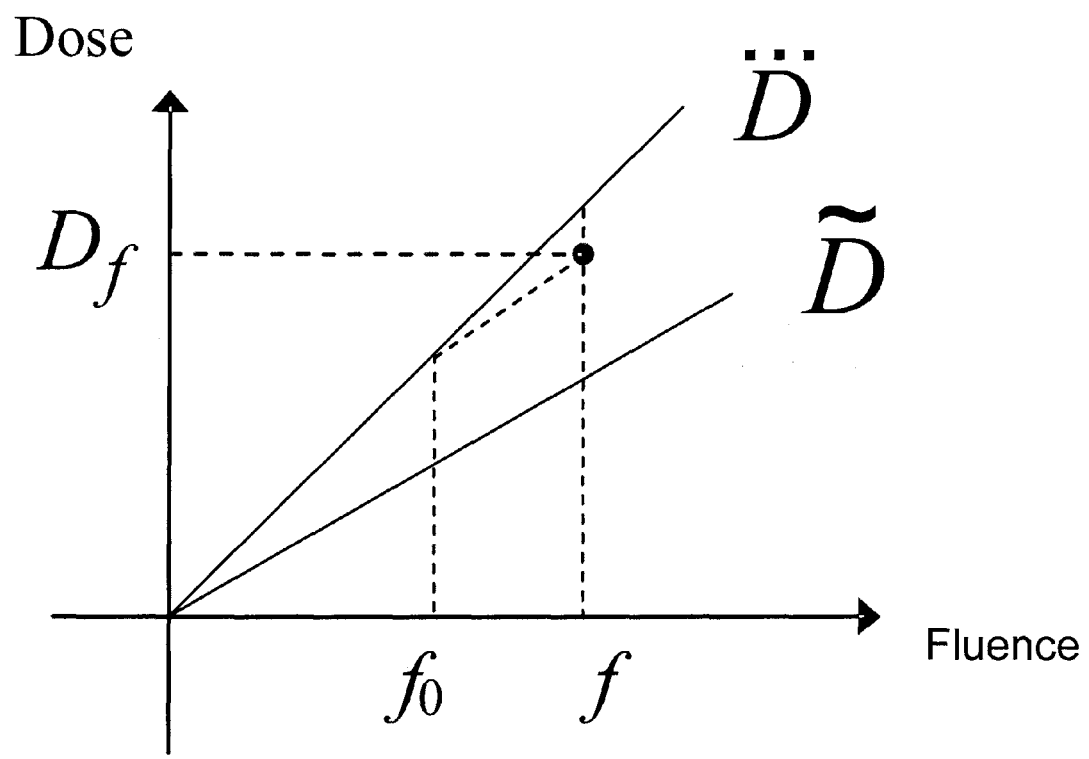
FIG. 9 is a pictorial illustration of correction-based dose update.

The idea behind the updated approximation is illustrated in FIG. 9. In particular, FIG. 9 provides a pictorial illustration of correction-based dose update. As shown in FIG. 9, the iteration dose $D_f$ approximates the full dose $\ddot{D}_f$ much better than the approximate dose $\tilde{D}_f$ does. Appendix B also provides a proof that the dose $D_f$ approximates the full dose $\ddot{D}_f$ with second order accuracy provided that $\tilde{D}_f$ approximates $\ddot{D}_f$ with first order accuracy. More precisely, if $|f-f_0| \leq \epsilon_1 f$ and $|\ddot{D}_f(x) - \tilde{D}_f(x)| \leq \epsilon_2 \ddot{D}_f(x)$, then $|\ddot{D}_f(x) - D_f(x)| \leq \epsilon_1 \epsilon_2 \ddot{D}_f(x)$. The second order accuracy of iteration dose $D_f$ greatly reduces the accuracy demand on the approximate dose $\tilde{D}_f$ and the frequency of full dose calculation. For example, if $\tilde{D}_f$ approximates the full dose $\ddot{D}_f$ within 10% and the difference between f and $f_0$ is also 10%, then the difference between the iteration dose $D_f$ and full dose $\ddot{D}_f$ is within 1% (=10%×10%).

To account for the scale difference that may exist between f and $f_0$ during optimization iteration, a slight variation is used to scale the correction term $\Delta D_{f_0}$ $$D_f = \tilde{D}_f + \lambda_1 \cdot \Delta D_{f_0} \quad (33)$$

by the scale factor $\lambda_1 = \|f\|/\|f_0\|$.

Moreover, to account for the systematic scaling difference between the full and approximate dose engines, the approximate dose $\tilde{D}$ can be replaced by $\lambda_2 \tilde{D}$, where $\lambda_2 = \|\ddot{D}_{f_0}\|/\|\tilde{D}_{f_0}\|$, and the above formula can then be followed to determine the iteration dose.

Note that the approximate dose engine $\tilde{D}_f$ is invoked whenever f changes. Therefore, the approximate dose is calculated once every iteration. On the other hand, the full dose engine $\ddot{D}_f$ is only called when the fluence f deviates from $f_0$ by a preset threshold $\|f-f_0\| > \epsilon \|f_0\|$. Then f replaces $f_0$, and the process continues. As optimization converges, the full dose will be calculated less and less frequently.

Also note that the derivative of iteration dose $D_f$ with respect to the fluence map is determined by the approximate dose only and is independent of the full dose. That is:

$$\frac{\partial D_f}{\partial f} = \frac{\partial \tilde{D}_f}{\partial f} \quad (34)$$

Such a feature makes the derivative calculation relatively easy, provided that the approximate dose $D_f$ has a simple formulation, which will be demonstrated below.

Although the MC method is regarded as being accurate in principle, its long computation time limits its use in routine clinical applications. C/S dose calculation is the standard dose engine in most TPSs and its accuracy for photon beam has been validated over the last decade. Some embodiments of the NVBB framework use CCCS as the as the full dose engine and the FCBB algorithm as the approximate dose engine. The full and approximate dose engines have the same first step $\vec{p} \to f$ but differ in the second step $f \to D$, which is the more time-consuming part. For example, in CCCS dose calculation, the second step is further divided into total energy release per unit mass ("TERMA") calculation and Convolution/Superposition. In FCBB dose calculation, this step is done by a simple distributive NVBB ray tracing, as will be described below.

i. Full Dose Calculation

C/S dose calculation consists of two independent parts: TERMA calculation and C/S energy deposition. TERMA calculation includes fluence phase space modeling, primary photon ray-tracing and modeling of the interaction with material, and TERMA sampling. C/S energy deposition is a means of spreading the released energy to the media by the pre-calculated MC kernels.

a. TERMA Calculation

With respect to TERMA calculation, recall the differential divergent beam shown in FIG. 7. The beam intersects the BEV plane at a point $P_0=(u,v,r_0)$ in BEV-CS with intersection area dudv. Suppose that the in-air energy fluence of X-ray is $f(u,v)$ at the BEV plane with normalized energy spectrum $\phi_0(E)(\int_0^{E_{max}}\phi_0(E)dE=1)$. Then the total energy for that infinitesimal beam is:

$$\Psi_0 = f(u,v)dudv \quad (35)$$

When the infinitesimal beam travels distance r through the media with energy dependent linear attenuation coefficient $\mu(E,t)$, the beam is attenuated and the spectrum becomes:

$$\phi(E)=\phi_0(E)\exp(-\int_0^r \mu(E,t)dt) \quad (36)$$

Let $\rho_e(t)$ be the electron density and define $$U(E,t) = \frac{\mu(E,t)}{\rho_e(t)}$$

as the (electron) mass attenuation coefficient. Note that for the range of energy in IMRT, the Compton effect dominates and $\mu(E,t) \propto \rho_e(t)$. That is, the (electron) mass attenuation coefficient has little material dependence $U(E,t) \approx U(E)$. Therefore, Equation (36) becomes:

$$\varphi(E) = \varphi_0(E)\exp\left(-U(E)\int_0^r \rho_e(t)dt\right) \quad (37)$$
$$= \varphi_0(E)\exp(-U(E)\hat{r}(r))$$

where $\hat{r}$ is the radiological distance defined as the integration of election density along the path of radiation beam:

$$\hat{r}(r)=\int_0^r \rho_e(t)dt \quad (38)$$

The total energy of that beam becomes:

$$\Psi(r)=\Psi_0\int_0^{E_{max}}\phi_0(E)\exp(-U(E)\hat{r}(r))dE \quad (39)$$

With the fact that $d\hat{r}/dr = \rho_e$, this makes the differential of $\Psi$ with respect to r:

$$\frac{d\Psi}{dr}(r) = -\Psi_0\rho_e(r)\int_0^{E_{max}}U(E)\varphi_0(E)\exp(-U(E)\hat{r})dE \quad (40)$$
$$= -\Psi_0\rho_e(r)A(\hat{r})$$

where $$A(\hat{r})=\int_0^{E_{max}}U(E)\phi_0(E)\exp(-U(E)\hat{r})dE \quad (41)$$

Note that $A(\hat{r})$ defines a material-independent lookup table for energy fluence attenuation with beam hardening correction. It can be calculated using the spectrum data $\{\phi_0(E)\}$ and the (electron) mass attenuation coefficients of water or fitted by dose commissioning procedures.

Recall that in the divergent beam geometry of FIG. 7, the energy $-d\Psi$ is released to the differential volume $dV=dudvdr/a(r)$ in BEV-CS. Also, recall that TERMA is the total energy released per unit mass, i.e.:

$$T = -\frac{d\Psi}{dm} = -\frac{d\Psi}{\rho dV} \quad (42)$$

Therefore, in BEV-CS, Equation (42) becomes:

$$T^*(u,r) = -\frac{a(r)d\Psi(r)}{\rho(r)\cdot dudvdr} \quad (43)$$
$$= f(u)a(r)A(\hat{r})\frac{\rho_e(r)}{\rho(r)}$$

With the approximation that electron density equals mass density $\rho_e \approx \rho$, Equation (43) becomes:

$$T^*(u,v,r)=f(u,v)A(\hat{r})a(r) \quad (44)$$

Accordingly, Equation (44) shows that the TERMA value at BEV-CS point (u,v,r) can be decomposed into three factors: fluence $f(u,v)$, divergence correction term $a(r)$, and beam hardening corrected attenuation term $A(\hat{r})$. Such decomposition makes TERMA easily calculated via ray tracing, as will be discussed below.

b. C/S Energy Deposition

The concept of cumulative-cumulative kernel ("CCK") can be adopted in the NVBB framework because of its implicit sampling accuracy. Therefore, instead of using tabulated kernels, the NVBB framework can use analytical kernels with two exponential components (exponential kernels). A separate optimization process can then be used to find the parameters of exponential kernels by fitting the tabulated kernels. A recursive formula can then be used for the CCK convolution. This reduces the complexity of C/S from $O(LN^4)$ to $O(LN^3)$, where L is the number of collapsed-cone directions and N is the number of spatial samples in each dimension. With exponential CCK kernels and high performance GPU implementation, the CCCS in NVBB framework is hundreds to thousands faster than its single thread CPU counterpart using tabulated CCK kernels.

ii. Approximate Dose Calculation

As discussed earlier, model-based dose calculation can be decomposed into two independent steps:

$$\vec{p} \xrightarrow{1} f \xrightarrow{2} D.$$

The first step is machine-dependent and requires accurate machine modeling, such as T&G, leakage, latency, etc. The first step is highly non-linear and sensitive to any modeling and calculation errors. In fact, errors in the first step propagate to the second step. Therefore, special attention should be paid to the first step to make the calculated dose match measurement regardless of how machine parameters change.

In addition, the fluence map also needs to be calculated using a grid fine enough to reduce sampling errors. Fortunately, the first step only involves one-dimensional or two-dimensional data, and, therefore, it has lower computation demands than the second step, which involves three-dimensional data. Because of its high importance and marginal computation demand, the NVBB framework can use accurate modeling and fine grids in the first step calculation. However, the second step, which models energy transportation in the patient body, is patient dependent. Therefore, the second step involves three-dimensional data and its computation demand is high such that special attention should be paid throughput. Full convolution/superposition is an accurate algorithm but is too time consuming to be used in every iteration. Therefore, the NVBB framework uses an approximate dose engine based on the FCBB algorithm that uses the same "fluence map calculation" as in the full C/S dose engine, but uses approximation in the second step.

In particular, given a fluence map, there are three main components that determine dose to the patient: beam divergence, fluence attenuation, and body scatter. Recall that full C/S dose calculation consists of two steps: TERMA calculation and C/S energy deposition. TERMA calculation models beam divergence and fluence attenuation. C/S energy deposition mainly models body scatter. Beam divergence is patient-independent, whereas both fluence attenuation and body scatter are patient (i.e., density) dependent. For the photon beam commonly used in radiotherapy, the heterogeneity correction is generally more important in the primary beam (fluence attenuation and forward/backward scatter) modeling than that in the secondary beam (lateral scatter) modeling. Based on the above analysis, the FCBB algorithm used in the NVBB framework decouples the three components (divergence, primary beam attenuation and scatter, and lateral scatter), applies heterogeneity correction only along the primary beam (analogous to fluence attenuation in TERMA calculation), and ignores the heterogeneity correction for lateral scatter contribution.

For example, the FCBB dose engine included in the NVBB framework is based on the fluence map without resorting to finite size pencil beams ("FSPB"). To describe FCBB, it is more expedient to use the BEV-CS.

As stated above, dose D(x) is linear with respect to the fluence map f. More precisely, the dose and the fluence map are related by the following integral:

$$D(x) = \iint f(u')B(x,u')du' \quad (45)$$

where B(x,u') is the dose distribution of the unit fluence irradiating on a infinitesimal area at u'. If (u,r) denotes the BEV coordinates of x, then the dose distribution B(x,u') can be decomposed approximately as a product of three dominant factors: the central axis contribution $c(\hat{r}(u', r))$, divergence correction a(r), and lateral spread function k(u−u') as follows:

$$B(x,u') \approx c(\hat{r}(u',r)) \cdot a(r) \cdot k(u-u') \quad (46)$$

where $\hat{r}(u',r)$ is the radiological distance from the source to (u',r):

$$\hat{r}(u',r) = \int_0^r \rho_e(u',r')dr' \quad (47)$$

and $\rho_e$ is the electron density function defined using the BEV coordinates. The central axis contribution $c(\hat{r}(u',r))$ can be approximated by $c(\hat{r}(u,r))$ for u close to u', and the lateral correction k(u−u') has fast fall-off. The divergence correction $a(r) = r_0^3/(r^2 s)$ is the Jacobian that accounts for the change of volume from the Cartesian-CS to the BEV-CS.

Substituting the approximation (46) into Equation (45), dose can be approximated as:

$$D(x) = \iint f(u')B(x, u')du' \quad (48)$$
$$\approx \iint f(u') \cdot c(\hat{r}(u, r)) \cdot a(r) \cdot k(u - u')du'$$
$$= c(\hat{r}(u, r)) \cdot a(r) \cdot \iint f(u')k(u - u')du'$$
$$= \tilde{D}^*(u, r)$$

Here the tilda ("~") stands for approximate dose and the superscript * stands for the BEV-CS.

Defining g to be the convolution of f and k yields:

$$g(u) = \iint f(u')k(u-u')du' \quad (49)$$

or simply $g = f \otimes k$, which makes the Equation (48):

$$\tilde{D}^*(u,r) = g(u) \cdot c(\hat{r}(u,r)) \cdot a(r) \quad (50)$$

Note that Equation (50) has the same format as Equation (44) for TERMA calculation. Therefore, the same TERMA calculation routine can also be used to calculate FCBB dose.

NVBB Derivative Calculation

Now that all of the tools used to derive formulas for derivative calculation have been described, given the objective functional $\Im(D) = \iiint F_D(x)dx$, the partial derivative of the objective with respect to the machine parameter $p_m$ can be calculated via the chain rule:

$$\frac{\partial \Im}{\partial p_m} = \iiint \frac{\partial F_D}{\partial D}(x) \cdot \frac{\partial D}{\partial p_m}(x)dx \quad (51)$$
$$= \iiint G_D(x) \cdot \frac{\partial D}{\partial p_m}(x)dx$$

where $G_D = \partial F_D/\partial D$, which is relatively easy to calculate from the definition of the objective functional. However, the term $\partial D/\partial p_m$ could be very complicated if explicitly calculated via the chain rule: $D = D_{\vec{p}}, \vec{p} = p_f$ $$\frac{\partial D}{\partial p_m}(x) = \iint \frac{\partial D}{\partial f_u}(x) \cdot \frac{\partial f_u}{\partial p_m} \cdot du \quad (52)$$

where $f_u = f(u,v)$.

If brute force is used, the calculation of the partial derivatives $\partial D/\partial f_{u,v}(x)$ will be extremely time consuming since it involves five-dimensional data (three-dimensions in x and two-dimensions in u). However, instead of explicitly calculating $$\frac{\partial D}{\partial p_m}(x), \frac{\partial F}{\partial \vec{p}}$$

can be directly calculated. In particular, with the NVBB ray tracing in the BEV-CS, $$\frac{\partial F}{\partial \vec{p}}$$

can be calculated in linear time ($O(N^3)$) per projection.

In particular, recall the iteration dose is calculated via adaptive full dose correction based on the following:

$$D_{\vec{p}}(x) = \tilde{D}_{\vec{p}}(x) + (\ddot{D}_{\vec{p}_0}(x) - \tilde{D}\vec{p}_0(x)) \quad (53)$$

where $\tilde{D}$ stands for approximate dose and $\ddot{D}$ stands for full dose. Accordingly, this yields:

$$\frac{\partial D}{\partial \vec{p}} = \frac{\partial \tilde{D}}{\partial \vec{p}} \quad (54)$$

Using the dose calculation formula in Equation (49) (i.e., $\tilde{D}^*(u,r)=c(\hat{r}(u,r))\cdot a(r)\cdot g(u)$), the derivatives with respect to the parameters $p_m$ can be derived as:

$$\frac{\partial D}{\partial p_m}(x) = \frac{\partial \tilde{D}^*}{\partial p_m}(u,r) \qquad (55)$$

$$= c(\hat{r}(u,r))\cdot a(r)\cdot \frac{\partial g}{\partial p_m}(u)$$

Letting:

$$h_m = \frac{\partial g}{\partial p_m} \qquad (56)$$

$$= \frac{\partial f}{\partial p_m} \otimes k$$

where $\partial f/\partial p_m$ is the derivative of fluence map with respect to the machine parameters (see equation definition above under "Fluence Map Modeling" section), yields:

$$\frac{\partial D}{\partial p_m}(x) = c(\hat{r}(u,r))\cdot a(r)\cdot h_m(u) \qquad (57)$$

Substituting Equation (57) in Equation (51) and switching to BEV coordinates, provides partial derivatives of the objective function with respect to the treatment parameters $\vec{p}$:

$$\frac{\partial \Im}{\partial p_m} = \int\int\int G_D(x)\cdot \frac{\partial D}{\partial p_m}(x)dx \qquad (58)$$

$$= \int\int\int G_D^*(u,r)\cdot c(\hat{r}(u,r))\cdot a(r)\cdot h_m(u)\cdot \frac{1}{a(r)}dudr$$

$$= \int\int\int G_D^*(u,r)\cdot c(\hat{r}(u,r))\cdot h_m(u)dudr$$

$$= \int\int h_m(u)\cdot \left(\int G_D^*(u,r)c(\hat{r}(u,r))dr\right)du$$

Furthermore, defining:

$$e_D(u)=\int G^*_D(u,r)\cdot c(\hat{r}(u,r))dr \qquad (59)$$

allows Equation (58) to be further simplified as:

$$\frac{\partial \Im}{\partial p_m} = \int\int h_m(u)\cdot e_D(u)du \qquad (60)$$

Note that the complex derivative computation $\partial\Im/\partial p_m$ is reduced to simple line integral (Equation (59)) and two-dimensional integral (Equation (60)). The line integral can be calculated by accumulative ray tracing and the two-dimensional integral can be calculated via simple summation, as will be described below.

Implementation i. Volume Discretization

In the previous sections about the NVBB framework, all functions, including the objective functional, fluence map, density, TERMA, dose, approximate dose, etc, are described in the continuous space. For the purpose of implementation, however, both inputs and outputs need to have finite, discrete representations.

Figure 10:
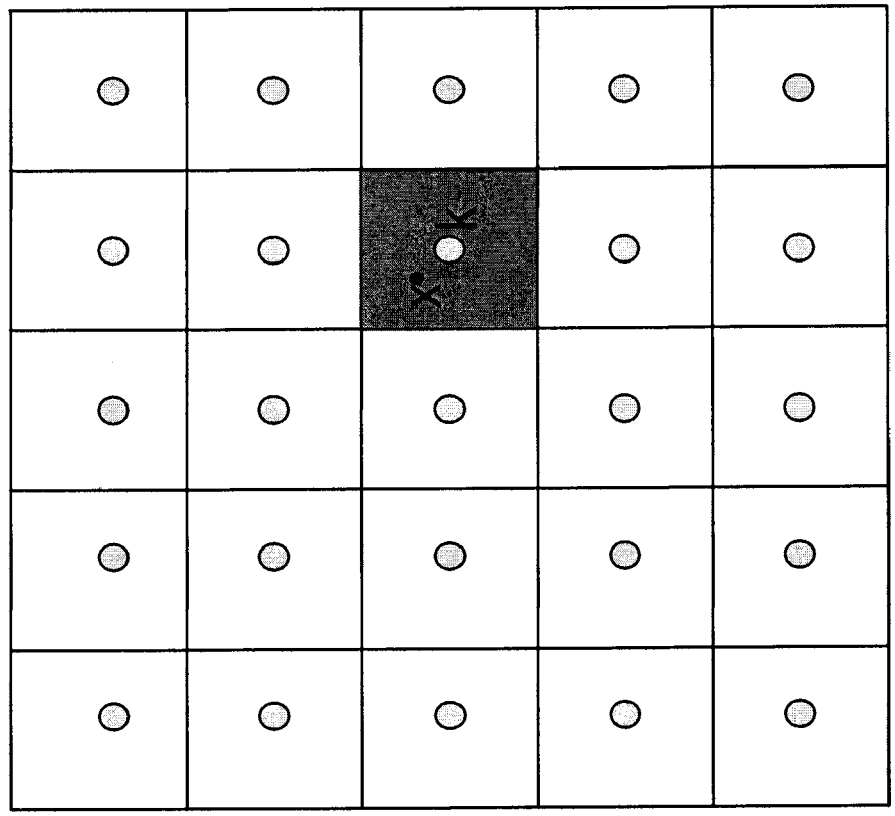
FIG. 10 schematically illustrates voxel representation.

There are two viewpoints for representing continuous images discretely: the voxel representation and grid representation. As described above, the voxel representation is commonly used in radiotherapy to discretize continuous space, and is used in the conventional VBS framework because of its analogy to pixels displayed in the screen. In voxel representation, a space is partitioned into cuboids of finite volume called voxels, and functions are constant within each voxel. That is, any point inside a voxel takes the same value:

$$f(x,y,z)=I(i,j,k), \text{ where } i=[x], j=[y], k=[z] \qquad (61)$$

where f(.) is a physical property, I is a discrete image, and [.] is the round operation. FIG. 10 illustrates voxel representation.

Figure 11:
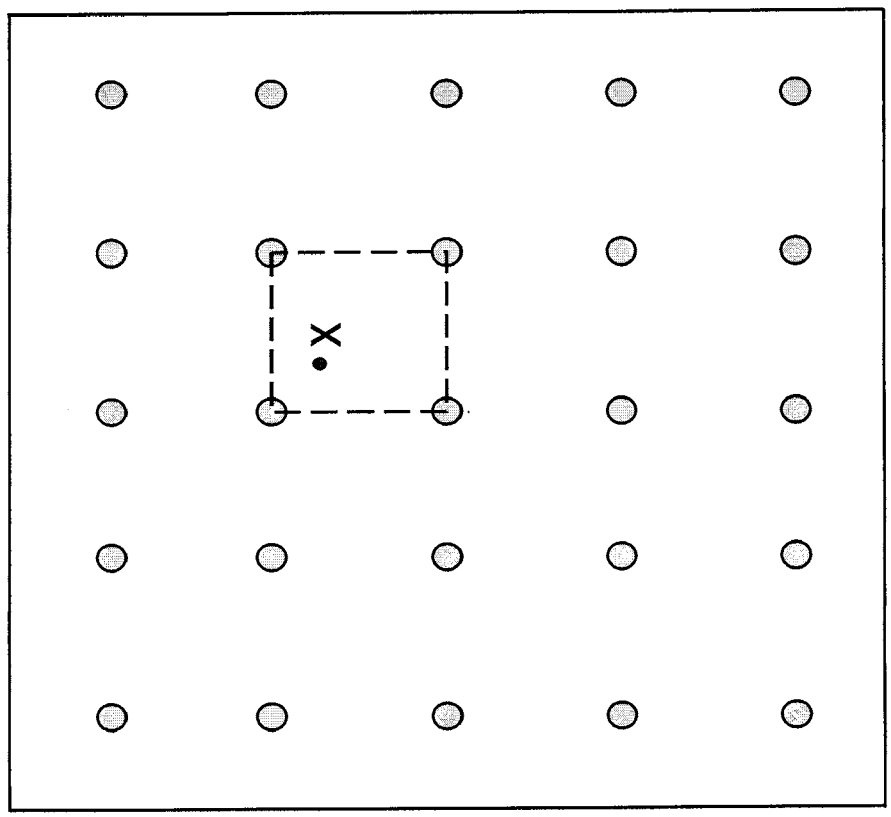
FIG. 11 schematically illustrates grid representation.

In grid representation, as illustrated in FIG. 11, a space is spanned by grid points of infinitesimal size. Each data point represents a sample in the continuous physical space, and the value at an arbitrary point is a weighted combination of grid values. That is:

$$f(x,y,z) = \sum_{i,j,k} a_{i,j,k} I(i,j,k) \qquad (62)$$

It can be seen that the voxel representation is a special case of the grid representation where the grid point is the voxel center and the weights are the coefficients for nearest neighbor interpolation. In this document, grid representation is adopted for its flexibility in modeling. Specifically, tri-linear interpolation is used to define $a_{i,j,k}$ in Equation (62):

$$f(x,y,z)=\Sigma_{i=\lfloor x\rfloor}^{\lfloor x\rfloor+1}\Sigma_{j=\lfloor y\rfloor}^{\lfloor y\rfloor+1}\Sigma_{k=\lfloor z\rfloor}^{\lfloor z\rfloor+1}a_{i,j,k}I_{i,j,k}$$

$$\text{where } a_{i,j,k}=(1-x+i)(1-y+j)(1-z+k) \qquad (63)$$

Note that $\lfloor . \rfloor$ stands for the "floor" operation. Also note that the interpolation given in Equation (63) is not limited to Cartesian grids. It can be applied to the BEV-CS as well. Linear interpolation can also used for conversion between Cartesian coordinates and BEV coordinates.

i. Ray Tracing

Ray tracing is widely used in physics to analyze optical or similar systems. The ray refers to a particle path. Ray tracing refers to a method that calculates and records the activity along a path followed by an advancing particle through regions of various characteristics that cause various particle reactions. In general, the rays can come from multiple sources and may change directions due to refraction, reflection, etc. As used in this document, the rays come from a single point source without direction changes. TERMA calculation is an example of point source ray tracing.

In TERMA calculation, the rays start from the source, go through a two-dimensional fluence map, and end with a three-dimensional TERMA distribution. Another type of ray tracing operation goes through a three-dimensional distribution and ends with a two-dimensional map. For example, the forward projection calculation (radon transform) in algebraic cone beam CT image reconstruction starts with a three-dimensional volume of attenuation coefficients and ends with two-dimensional projection data (detector signal). Generally, ray tracing can be divided into two groups according to its operation type: distributive ray-tracing and accumulative ray-tracing. Distributive ray-tracing, such as TERMA calculation, goes from a lower dimension to higher dimension, e.g. from two-dimensional (input) to three-dimensional (output).

On the other hand, accumulative ray-tracing, such as projection calculation, goes from a higher dimension to lower dimension, e.g. from three-dimensional (input) to two-dimensional (output). Distributive ray tracing, as the name suggests, distributes physical properties, such as energy, along the ray into the medium, while accumulative ray tracing accumulates physical properties of the medium along the ray to the reference plane.

ii. Voxel-Based Ray Tracing

Figure 13:
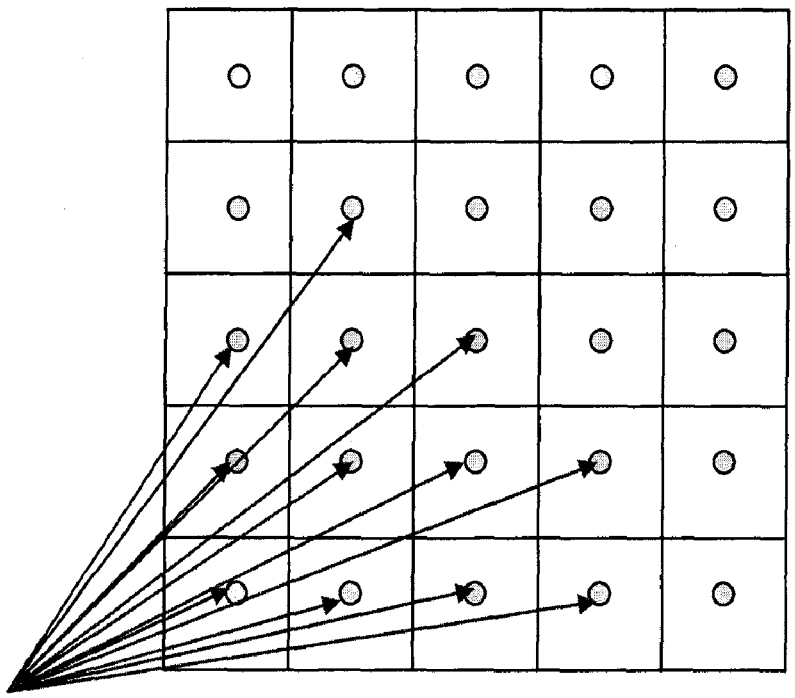
FIG. 13 schematically illustrates voxel-based voxel-driven ray tracing for a two-dimensional case.
Figure 12:
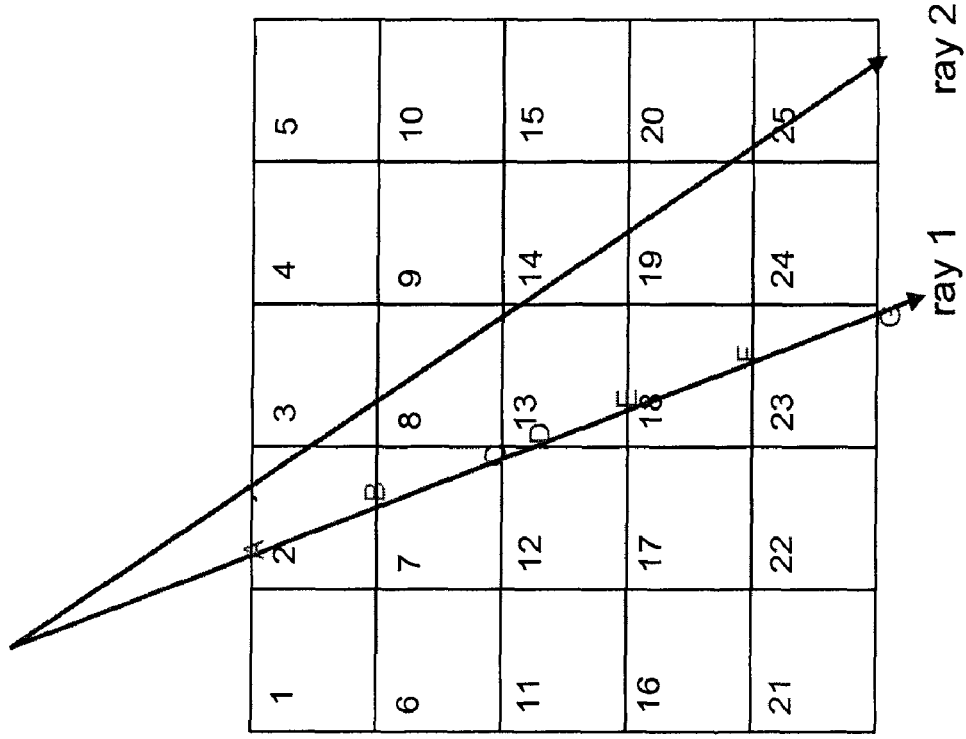
FIG. 12 schematically illustrates voxel-based ray-driven ray tracing for a two-dimensional case.

Distributive-ray-tracing can be used in TERMA calculation. In voxel-based TERMA calculation, the radiation energy is transported from a point source to patient volume that is cut into voxels of finite size. Similar to that in CT image reconstruction, there are generally two categories of ray tracing for voxel-based geometry: ray-driven tracing and voxel-driven tracing. FIG. 12 schematically illustrates voxel-based ray-driven ray tracing for a two-dimensional case, and FIG. 13 schematically illustrates voxel-based voxel-driven ray tracing for a two-dimensional case. For both ray tracing methods, the tracing-ray that originates from the point source is a line of zero width (the arrowed lines in FIGS. 12 and 13), and the effect of beam divergence is explicitly accounted for through ray tracing.

In ray-driven tracing, every voxel that is visited (intersected) by the tracing ray gets some share. For example, ray 1 illustrated in FIG. 12 intersects voxel 2, 7, 12, 13, 18, 23 with intersection points A, B, C, ... G. The line segments, AB, BC, CD, ... FG are used to calculate the radiological distance within the voxel. Brute force calculation of intersection voxels and intersection points may be quite time consuming. Some algorithms, such as Siddon list, have been proposed to save computation time. In addition, the ray samples must be fine enough to make sure the farthest voxels are visited at least once. If the ray sampling is too coarse, a voxel may not be visited by any ray, which results in significant artifacts in dose calculation. For example, voxel 24 in FIG. 12 is not visited by any rays and its TERMA value will be zero, which causes a significant artifact. As also illustrated in FIG. 12, a voxel may be visited by multiple rays (e.g. voxel 13 is visited by both ray 1 and ray 2), and, therefore, various voxel normalizations must be used to weigh the contributions of each ray and the TERMA value may be sensitive to the normalization methods chosen. In addition to the issues of insufficient sampling and normalization artifacts, "write-write conflicts" may occur, because each voxel can receive contributions from multiple rays and different rays executed by different threads may attempt to write to the same voxel at the same time, which is a typical scenario in parallel computation, such as when using a GPU for ray tracing. Resolving write-write conflicts may be very costly and thus may significantly impede performance. For example, for a three-dimensional image of size $N^3$, the number of rays in ray-driven tracing is $O(N^2)$ and the number of intersections is $O(N)$ per ray, which results in the complexity of $O(N^3)$.

To overcome the normalization artifacts and the write-write conflict issues of ray-driven tracing, the voxel-driven method (see FIG. 13) is sometimes used, especially in the case of parallel implementations. Voxel-driven tracing has better sequential memory access pattern and no write-write conflicts. However, because each voxel corresponds to one ray, the number of rays is $O(N^3)$ and the complexity of whole tracing algorithm is $O(N^4)$, which is highly undesirable for any decent size of N. In addition, the fluence map sampling in voxel-based tracing is unevenly spaced, which makes it hard to maintain energy conservation in ray sampling.

iii. NVBB Ray Tracing

Figure 14:
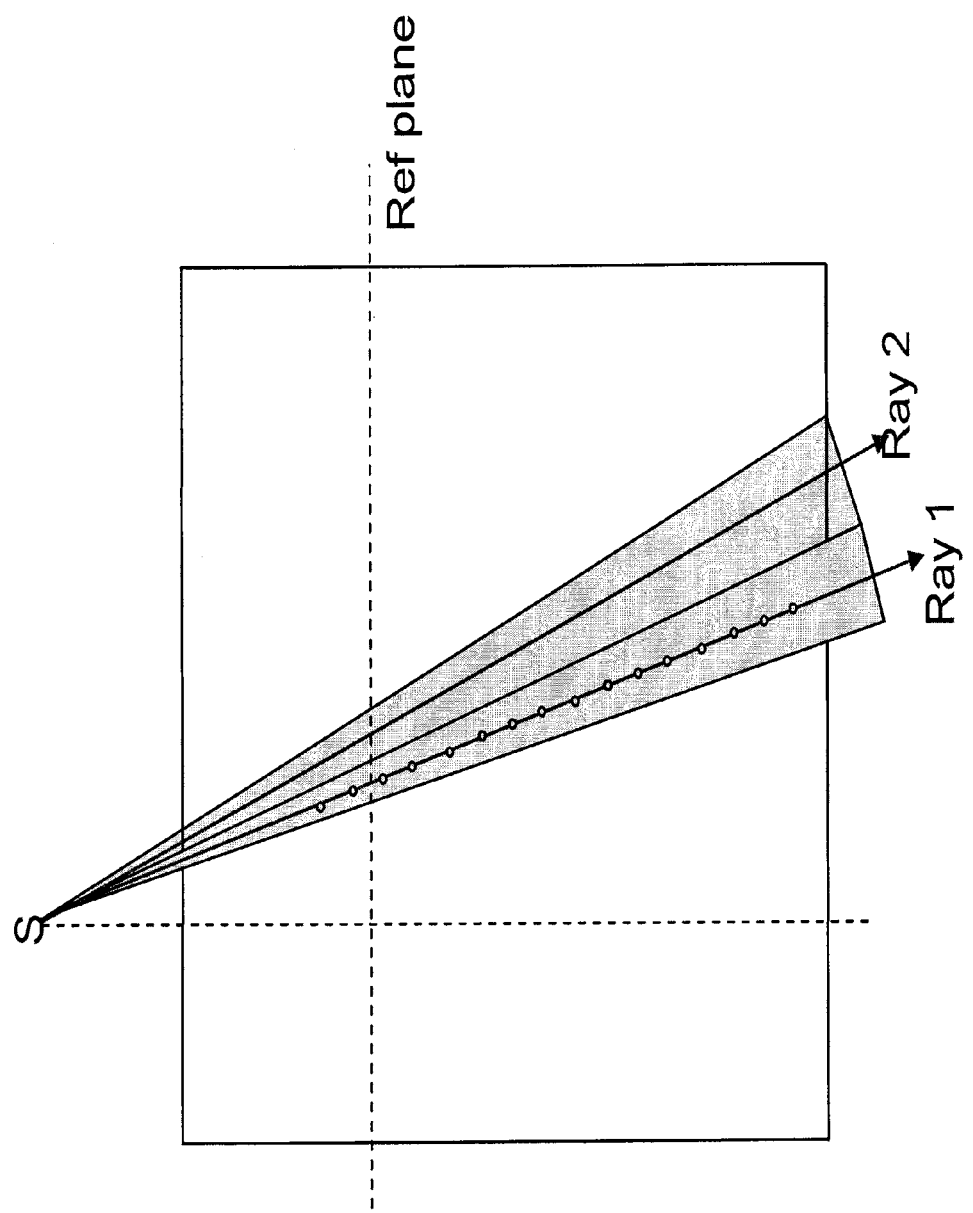
FIG. 14 illustrates non-voxel-based broad-beam ray tracing in two dimensions.

FIG. 14 illustrates NVBB ray tracing in two dimensions. Space is regarded as continuous, and each ray represents a narrow pyramid (e.g., a triangle for two-dimensional illustrations) with the vertex at the source position. Each spatial point is covered by one and only one such pyramid, and the samples are along the central axis of the ray pyramid.

Unlike voxel-based ray tracing, where the space discretized as stacked voxels and ray tracing is defined and operated in Cartesian coordinates, NVBB ray tracing regards the three-dimensional space as continuous and ray tracing is operated in BEV coordinates. In voxel-based ray tracing, the tracing ray is an infinitesimally narrow line, while its physical counterpart is divergent in nature. Therefore, beam divergence must be additionally accounted for during voxel-based ray tracing. Furthermore, because each ray comes from only one sample of the fluence map, special care is needed to maintain energy conservation of the fluence map in the sampling operation, especially when the fluence map is non-evenly sampled. On the other hand, in NVBB ray tracing, the tracing ray is represented by a narrow pyramid with the source being the vertex, which naturally depicts a physical divergent beam of finite size, as illustrated in FIG. 7. Beam divergence is implicitly accounted for in BEV coordinates. The space occupied by this ray pyramid gets contributions from the tracing ray. Each ray pyramid carries the energy from the cross-section of the pyramid by the fluence map, and therefore, energy conservation is implicitly maintained even if the fluence map is non-evenly partitioned.

For NVBB ray tracing, only u and r need to be sampled. The sampling of u defines the cross sections of the ray pyramids by the reference plane and can be evenly or unevenly spaced. For a continuous two-dimensional function f(u,v) (e.g. fluence map), the sample $\bar{f}(u_i,v_j)$ can be defined as the mean over the area $\Delta u_i \Delta v_j$:

$$\bar{f}(u_i, v_j) = \frac{1}{\Delta u_i \Delta v_j} \int_{u_i - \frac{\Delta u_i}{2}}^{u_i + \frac{\Delta u_i}{2}} \int_{v_j - \frac{\Delta v_j}{2}}^{v_j + \frac{\Delta v_j}{2}} f(u, v) \, du \, dv \quad (64)$$

For ease of implementation, a regular Cartesian grid is recommended for sampling u. If uneven sampling is preferred, the sampling steps should mainly be determined by the gradient of the fluence map. Sampling should be fine in the high gradient region and coarse in the flat region. Furthermore, u sampling should also consider the gradient of the three-dimensional volume to better account for heterogeneous regions. However, no matter what kind of sampling methods are used, the nature of NVBB ray tracing eliminates systematic errors from normalization and point missing artifacts. The r sampling is along the central axis of the ray pyramid. Equal-distant sampling of r, comparable to the original CT resolution, is recommended to avoid missing heterogeneity.

In this document, distributive-ray-tracing is used for TERMA calculation and FCBB dose calculation, and accumulative-ray-tracing is used to calculate partial derivatives of the objective functional in the NVBB framework.

Recall that the TERMA calculation formula $T^*(u,v,r)=f(u,v)A(\hat{r}(u,v,r))a(r)$ and the FCBB dose formula $\tilde{D}^*(u,v,r)=g(u,v)c(\hat{r}(u,v,r))a(r)$ can be generally implemented as distributive-ray-tracing as described below in Table 1.

TABLE 1

Distributive Ray Tracing

| | |
|---|---|
| Inputs: | ρ(x): three-dimensional density function defined on a Cartesian grid |
| | f(u): two-dimensional distribution defined in the reference plane |
| | A($\hat{r}$): one-dimensional radiological-distance-dependant LUT |
| Outputs: | F*(u,r): three-dimensional distribution defined in BEV coordinates |

Function F = DistributiveRayTracing(f, A, ρ)
Foreach u = (u,v) on the reference plane (do in parallel)
    For each r
        Calc radiological distance $\hat{r}$+ = ρ*(u,$\hat{r}$)Δr
        F*(u, r) = f(u)A($\hat{r}$)a(r)
    Endfor
Endfor The calculation of derivative $e_D(u) = \int G^*_D(u,r) \cdot c(\hat{r}(u,r))dr$ can also be implemented as accumulative-ray-tracing as described below in Table 2.

TABLE 2

Accumulative Ray Tracing

| | |
|---|---|
| Inputs: | G(x): three-dimensional distribution defined in Cartesian grid |
| | ρ(x): three-dimensional density function defined in Cartesian grid |
| | A($\hat{r}$): one-dimensional radiological-distance-dependant LUT |
| Outputs: | $\bar{g}$(u): two-dimensional distribution defined on the reference plane |

Function g= AccumulativeRayTracing(G,A,ρ)
For each u = (u,v) on the reference plane (do in parallel)
    $\bar{g}$(u):= 0, $\hat{r}$ := 0
    Foreach r
        Calc radiological distance $\hat{r}$+ = ρ*(u,r)Δr
        $\bar{g}$(u)+ = G* (u,r)A($\hat{r}$)dr
    Endfor
Endfor Note that in general, the inputs of three-dimensional distributions are defined on the Cartesian grid. Therefore, to evaluate ρ*(u,r) (and G*(u,r) in accumulative operation), a BEV to Cartesian coordinate conversion is needed using tri-linear interpolation. That is:

$$\rho^*(u,r) = \rho(P) \quad (65)$$

where $P = ue_u + ve_v + (r-r_0)e_r$ as defined in Equation (6) and described below in Table 3.

TABLE 3

BEV to Cartesian transform

| | |
|---|---|
| Inputs: | source position S and reference plane |
| | F* (u,r): three-dimensional distribution defined in BEV-CS |
| Outputs: | F(x): three-dimensional distribution defined in Cartesian CS |

Function F= BEV-to-Cartesian-transform (F*)
    Foreach x = (x,y,z) in Cartesian coordinate system (do in parallel)
    Calculate u,r as in Eq. (8)
F(x) = F*(u,r)
Endfor Note that in the accumulative operation, the results of accumulation g(u) are defined on the reference plane (i.e. the fluence map plane) and samples are in Cartesian grid. Therefore, no further coordinate conversion is needed for g. In the distributive operation, the results of distribution F*(u,r) are in the BEV-CS. However, because many evaluations, e.g. dose volume histogram (DVH) calculation, are done in the three-dimensional Cartesian-CS, a conversion involving tri-linear interpolation from the BEV-CS to the Cartesian-CS as given in Equation (6) may be used.

Although evenly spaced sampling is proposed for both u and r in NVBB ray tracing, in principle, sampling can be arbitrarily spaced, provided that the samples are fine enough for high gradient regions of the input data. There are no missing voxel artifacts nor normalization requirements, as every spatial point is covered by one and only one ray pyramid, and energy conversion is always maintained.

iv. Implementation of the NVBB Framework

Figure 15:
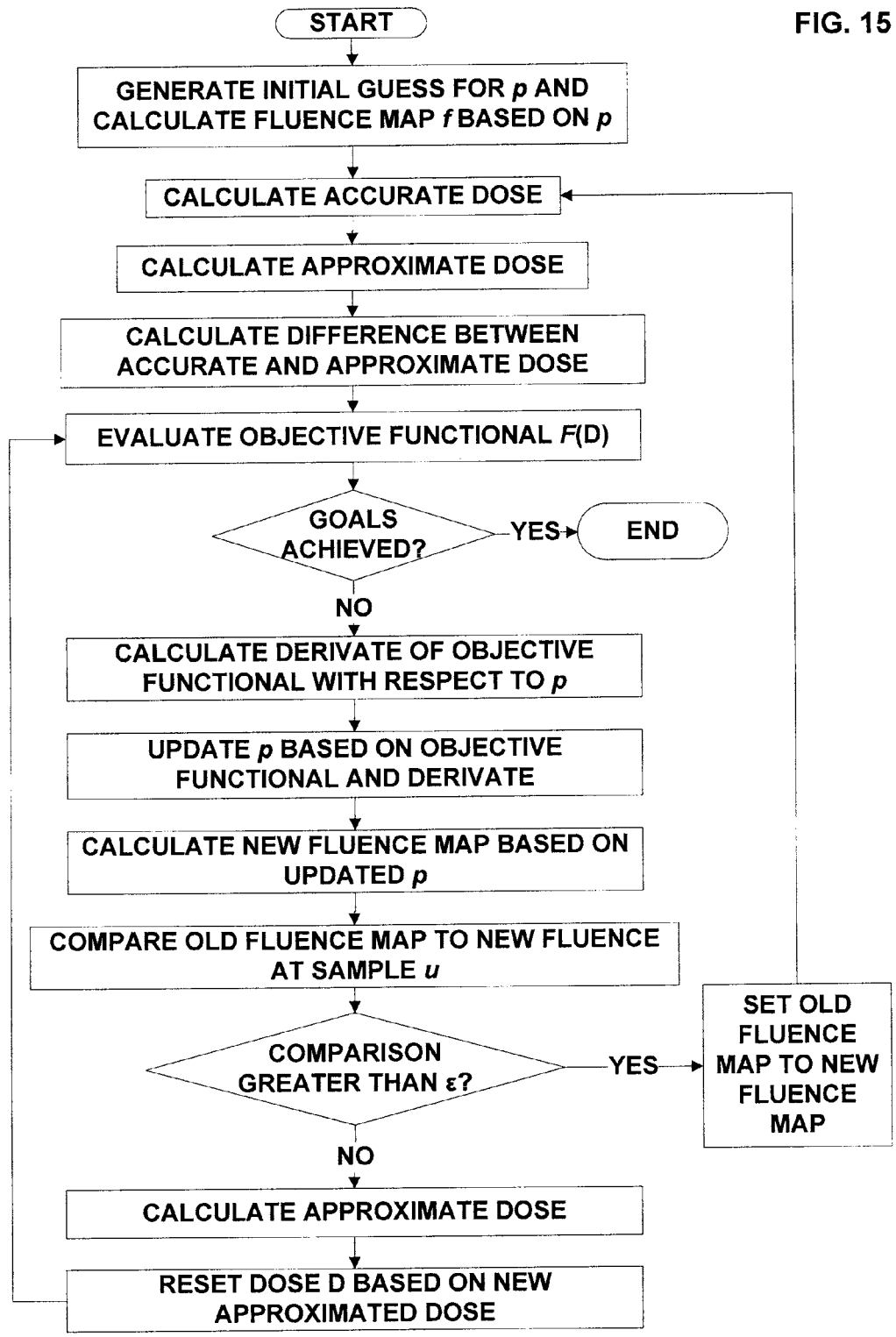
FIG. 15 is a flow chart schematically representing a non-voxel-based broad-beam framework for intensity modulated radiation therapy optimization.

Now that the building blocks for the NVBB framework have been described, the methods for the NVBB framework are summarized in this section. In particular, the NVBB framework for IMRT optimization is illustrated in FIG. 15 and described below in Table 4.

TABLE 4

Pseudo code of the NVBB framework for IMRT optimization

1. Generate an initial guess for $\vec{p} = \vec{p}_0$ and calculate the fluence map $f = f_0 = f_{\vec{p}_0}$.

2. Calculate accurate dose $\ddot{D}_{f_0}$,

3. Calculate approximate dose $\tilde{D}_{f_0}$

4. Calculate difference $\Delta D_{f_0} = \ddot{D}_{f_0} - \tilde{D}_{f_0}$

5. Evaluate the objective $\mathcal{J}(D)$.

6. If the clinical goal achieved, return.

7. calculate derivative $\partial \mathcal{J} / \partial \vec{p}$

8. Update $\vec{p}$ based on $\mathcal{J}$ and $\partial \mathcal{J} / \partial \vec{p}$.

9. Calculate the fluence map $f = f_{\vec{p}}$

10. If $\frac{|f(u) - f_0(u)|}{|f_0(u)|} > \varepsilon$ let $f_0 = f$ and go to 2.

11. Calculate approximated dose $\tilde{D}_f$

12. Let $D = \tilde{D}_f + \frac{\|f\|}{\|f_0\|} \Delta D_{f_0}$ and go to 5.

The approximate dose $\tilde{D}_f$ used in the above code is the FCBB dose described above. The implementation of approximate dose calculation (in pseudo code) is also described below in Table 5.

TABLE 5

Pseudo code for approximate dose calculation

Inputs:

$\vec{p}$: machine parameters
ρ: three-dimensional density distribution in Cartesian grid
c: one-dimensional CAX-LUT
k: two-dimensional lateral convolution kernel Outputs:

$\tilde{D}$: three-dimensional approximate dose distribution in Cartesian grid
Function $\tilde{D}$ = FCBB__Dose($\vec{p}$,ρ,c,k)
    calculate fluence map $f = f_{\vec{p}}$
    calculate g = f ⊗ k
    $\tilde{D}^*$ = DistributiveRayTracing (g,c,ρ)
    $\tilde{D}$ = BEVtoCartesian($\tilde{D}^*$)

The full dose is the CCCS dose calculation method described above. The same distributive-ray-tracing as FCBB dose calculation can be used for TERMA calculation. That is, TERMA is first calculated in the BEV-CS via NVBB ray tracing and then converted to the Cartesian-CS with tri-linear interpolation. The implementation of the full dose calculation (in pseudo code) is described below in Table 6.

TABLE 6

Pseudo code for full dose calculation

Inputs:

$\vec{p}$: machine parameters
$\rho$: three-dimensional density distribution in Cartesian grid k
A: fluence attenuation table
K: collapsed-cone convolution kernel Outputs:

$\ddot{D}$: three-dimensional accurate dose distribution in Cartesian grid

Function $\ddot{D}$ = CCCS_Dose($\vec{p}$, $\rho$, A, K)
    calculate fluence map $f = f_{\vec{p}}$
    T* = DistributiveRayTracing (g, A, $\rho$);
    T = BEVtoCartesian (T*);
    $\ddot{D}$ = CCCS(T, $\rho$, K)

Implementation of CCCS energy deposition (the last function call in Table 6) using cumulative-cumulative tabulated and exponential kernels and parallelization using CPUs and GPUs were described in Lu W., Olivera G. H., Chen M., Reckwerdt P. J., and Mackie T. R., *Accurate Convolution/Superposition for Multi-Resolution Dose Calculation Using Cumulative Tabulated Kernels*, PHYSICS MED. BIOLOGY, 2005, at 50, 655-80 and Chen Q., Chen M., and Lu W., *Ultrafast Convolution/Superposition Using Tabulated and Exponential Cumulative-Cumulative-Kernels on GPU*, XVITH INTERNATIONAL CONFERENCE ON THE USE OF COMPUTERS IN RADIO THERAPY, 2010.

As for the partial derivative calculation, the calculation of $e_D(u) = \int G^*_D(u,r) \cdot c(\hat{r}(u,r)) dr$ is done by the "AccumulativeRayTracing" function as described in Table 2, and the calculation of $\partial \Im / \partial p_m = \iint h_m(u) e_D(u) du$ is done by the following two-dimensional summation:

$$\frac{\partial \Im}{\partial p_m} = \int \int h_m(u) e_D(u) du \quad (66)$$

$$= \sum_{i,j} h_m(u_i, v_j) \bar{e}_D(u_i, v_j) \Delta u_i \Delta v_j$$

The pseudo code for calculating partial derivates is also described below in Table 7.

TABLE 7

Pseudo code for partial derivative calculation

Inputs:

D: three-dimensional dose distribution
$F_D$: objective function

Outputs:

$\partial \Im / \partial \vec{p}$: partial derivatives with respect to machine parameters
    calculate $G_D = \partial F_D / \partial D$
    calculate $\bar{e}_D$ = AccumulativeRayTracing ($G_D$, c, $\rho$)
    for each parameter m (do in parallel)
        a. calculate $h_m = \partial g / \partial p_m$
        b. calculate $\partial \mathcal{J} / \partial p_m = \sum_{i,j} h_m(u_i, v_j) \bar{e}_D(u_i, v_j) \Delta u_i \Delta v_j$ Complexity Analysis The problem size of the conventional VBS framework is determined by the product of the number of voxels and the number of beamlets. Let the number of samples along any direction be N and assume the bixel size is comparable to the voxel size. Then the number of voxels is $M = O(N^3)$ and the number of beamlets is $K = O(N^2)$ for every beam angle. Therefore, the size of the B matrix is $MK = O(N^5)$. Therefore, the VBS framework has a spatial complexity of approximately $O(N^5)$.

In the VBS framework, two time-consuming operations in every iteration are the dose calculation $\vec{d} = B\vec{w}$ and the derivative calculation $$\frac{\partial \Im}{\partial \vec{w}} = B^t \frac{\partial \Im}{\partial \vec{d}},$$

where the vector $\vec{w}$ has a length of K, $$\frac{\partial \Im}{\partial \vec{d}}$$

has a length of M, and both matrix multiplications have complexity of $O(MK) = O(N^5)$. Therefore, in the VBS framework, both spatial and temporal complexities of the system are $O(N^5)$. Various compression techniques can be used to reduce the problem size to $O(N^5/R)$, where R is the compression ratio. However, this $O(N^5)$ complexity limits the usage of the VBS framework in applications that require fine resolution (i.e., large N, such as N=256 or 512).

In the NVBB framework, since both dose and derivatives are calculated on the fly through distributive or accumulative ray tracing, no B matrix is required. Therefore, the spatial complexity is $O(N^3)$ to store the three-dimensional volume such as density, TERMA, dose, etc. In every iteration of NVBB optimization, there are two NVBB ray-tracing operations that are time consuming. The first operation is calculating approximate dose in the BEV coordinate system via distributive ray tracing (i.e., $D^*(u,r) = c(\hat{r}(u,r)) \cdot a(r) \cdot g(u)$), and the second operation is calculating derivatives via accumulative ray tracing (i.e., $e_D(u) = \int G^*_D(u,r) \cdot c(\hat{r}(u,r)) dr$).

Suppose that the fluence map sampling and ray sampling have the same resolution as the three-dimensional volume. Then the number of rays is $O(N^2)$ and the number of samples per ray is $O(N)$, and, therefore, the complexity of both ray-tracing operations is $O(N)*O(N^2) = O(N^3)$.

There are several other three-dimensional operations, including calculation of $G_D(x)$, converting the approximate dose in BEV-CS to Cartesian-CS $\tilde{D}(x) = \tilde{D}^*(u,r)$, and full dose correction $D(x) = \tilde{D}(x) + \Delta D_0(x)$. All of these operations have a complexity proportional to the number of dose samples (i.e., $O(N^3)$).

In the NVBB framework, full CCCS calculations are performed every few iterations when the difference between f and $f_0$ is above a certain threshold. Typically, the CCCS dose calculation happens more frequently at the beginning and less frequently as the solution converges. The TERMA part of CCCS uses distributive-ray-tracing, and thus it also has complexity of $O(N^3)$. The convolution/superposition part typically takes 5-10 longer than TERMA calculation. That is, a full dose iteration is about an order of magnitude more expensive than other iterations. However, the frequency of full dose iteration is an order of magnitude less than that of approximate dose and derivative calculation. Therefore, in general, including full dose correction at most doubles the total iteration time as compared to using approximation dose for iteration.

Other operations in the NVBB framework involve one-dimensional or two-dimensional data with complexity of $O(N)$ or $O(N^2)$, which can be omitted compared with the $O(N^3)$ complexity.

In summary, both the temporal complexity and spatial complexity for the NVBB framework in IMRT optimization are linear with respect to dose samples ($O(N^3)$ for $N^3$ spatial samples), and linear complexity makes it easier to handle large systems (e.g., $N \geq 256$).

Note that the NVBB framework as described in Tables 1 to 7 or portions thereof can be implemented in parallel. For example, the parallelized parts of the algorithm are indicated as "do in parallel" in the pseudo code. The parallelized parts can be efficiently implemented in GPUs for various reasons. First, the linear spatial complexity $O(N^3)$ allows the problem to fit in the small memory of GPU, even for a large case (N>=256). For example, for a large dose grid of 256×256×256, the amount of memory needed for every three-dimensional volume is 64 megabytes ("MB"). Suppose up to ten three-dimensional volumes (density, TERMA, full dose, derivatives, . . . ) need to be internally stored. Then the memory requirement is only 640 MB, which can still fit in a modern GPU card with global memory around 1 GB. In addition, the fully parallelizable nature of NVBB ray tracing makes it easy to maintain instruction and data alignment. Also, there is no data write-write-conflict in any part of the parallelized code, and tri-linear interpolations are inherently implemented via texture structures in modern GPUs with little cost.

Results

An example NVBB framework was implemented in the C++ programming language on both CPU and GPU architectures. The CPU implementation used a message passing interface ("MPI") for parallelization. The GPU implementation used the NVIDIA CUDA™ architecture for intra-GPU parallelization and used MPI for inter-GPU communication. Both the CPU and GPU implementations were incorporated into the TomoTherapy® TPS. The CPU version ran on a computer cluster and the GPU version ran on a single workstation with a NVIDIA GeForce GTX 295 graphic card.

Verification and validation tests were performed both internally and externally. Benchmarks on dose accuracy, planning quality, and throughput were also collected and compared with the current cluster-based TomoTherapy® TPS that uses a VBS framework. Table 8 summarizes comparisons between the NVBB framework on a workstation with a 2.66 GHz CPU and one NVIDIA GeForce GTX 295 card (the "NVBB-GPU" implementation) and the VBS framework on a Tomo-Therapy® 14-node cluster (14×4=56 2.66 GHz CPUs) (the "VBS-cluster" implementation). All times indicated in Table 8 are in seconds.

As illustrated above, Table 8 summarizes performance comparisons between the VBS-cluster and the NVBB-GPU for various clinical cases. The reported times are the preprocessing time, the time for performing 100 iterations, and the time for calculating the full dose and the final dose. The total time is the summation of the previous four times. With the

TABLE 8

Clinical Comparisons

| Cases | Dose Grid Size | No. of Beamlets | TPS | Pre-processing | 100 Iterations | Full Dose | Final Dose | Total Time |
|---|---|---|---|---|---|---|---|---|
| prostate | 328 × 268 × 35 | 4830 | VBS-cluster | 585 | 300 | 52.4 | 73.4 | 1010.8 |
| | | | NVBB-GPU | 10 | 250 | 7.2 | 7.4 | 274.6 |
| lung | 128 × 134 × 114 | 11827 | VBS-cluster | 1000 | 257 | 46.9 | 64 | 1367.9 |
| | | | NVBB-GPU | 10 | 205 | 5 | 5.6 | 225.6 |
| breast | 144 × 128 × 176 | 14631 | VBS-cluster | 1300 | 420 | 46.4 | 66.4 | 1832.8 |
| | | | NVBB-GPU | 10 | 180 | 4.4 | 4.6 | 199 |
| H&N | 256 × 256 × 125 | 8121 | VBS-cluster | 1489 | 491 | 82.7 | 170.8 | 2233.5 |
| | | | NVBB-GPU | 10 | 403 | 12.5 | 12.6 | 438.1 |
| TBM | 144 × 128 × 176 | 117027 | VBS-cluster | 6785 | 1745 | 153.3 | 210.7 | 8894 |
| | | | NVBB-GPU | 10 | 526 | 13 | 13.1 | 562.1 | current VBS-cluster, a typical TomoTherapy® planning took 10 to 100 minutes to pre-calculate beamlet doses. The preprocessing times were reduced to about 10 seconds with the NVBB-GPU. Excluding the preprocessing time, the NVBB-GPU took only about 30% to 90% of the iteration time of the VBS-cluster for the same number of iterations. As for the full dose and the final dose calculation, the NVBB-GPU has a speedup of about 8 to 16 times over the VBS-cluster.

Both the VBS-cluster and the NVBB-GPU used CCCS as the full and final dose engine. The number of collapsed-cone directions are 24 (zenith)×16 (azimuth)=384. The VBS-cluster used tabulated CCK, while the NVBB-GPU uses exponential CCK. For the same delivery plans, the differences of final dose between the VBS-cluster and the NVBB-GPU are within 1% (e.g., 1 millimeter for all test cases), while the doses of the VBS-cluster were well commissioned to match the measurements.

Figure 16:
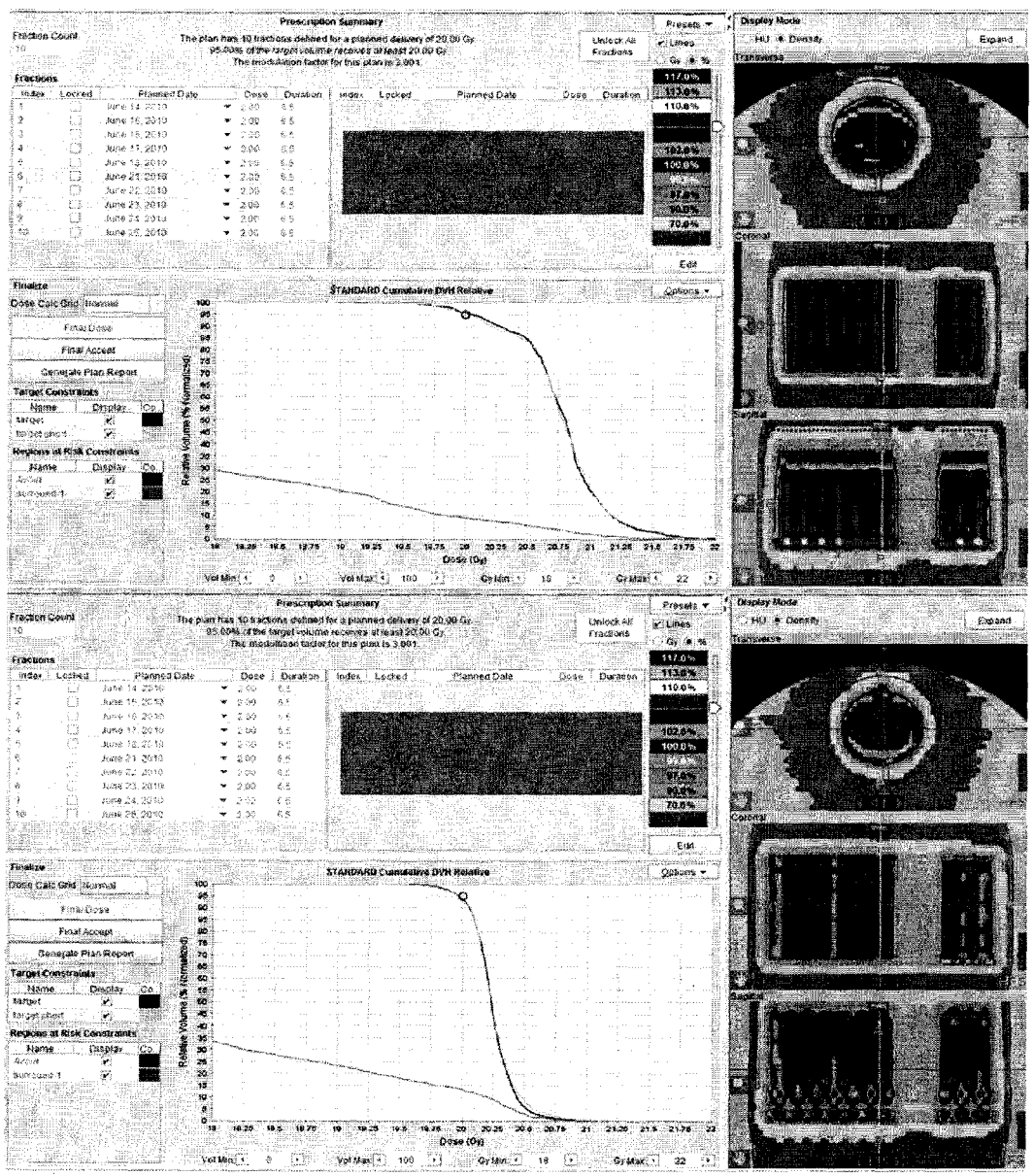
FIG. 16 illustrates comparisons of final doses calculated using a cluster of computers implementing a voxel-based beamlet superposition framework and a graphics processing unit implementing a non-voxel-based broad-beam framework.

For most cases, after the same number of iterations, the plan quality under these two TPS implementations had no clinically significant differences, except for some cases where the NVBB-GPU showed superior plan quality over the VBS-cluster. FIG. 16 illustrates one such case. The case illustrated in FIG. 16 is a case of "running start/stop (RSS)" TomoTherapy® plan for two separate targets (17 centimeters off axis) with maximum jaw width of 5 centimeters, pitch of 0.2, and modulation factor of 3. The targets' far off-axis positions caused this case to be hard to be optimize due to the large thread effect. The top panel illustrated in FIG. 16 shows the final dose after 100 optimization iterations with the VBS-cluster, while the bottom panel shows the final dose after the same number of iterations with the NVBB-GPU. Note that the x-axes of both DVHs are zoomed-in to demonstrate the differences. Both DVH and dose distribution show that the final dose of the VBS-cluster has much less dose uniformity than that of the NVBB-GPU. This inferior plan quality of the VBS-cluster is due to its model limitation and the errors from beamlet calculation and compression. The DTPO and the non-voxel, non-beamlet nature of the NVBB framework greatly reduces these modeling errors, which results in a better plan.

SUMMARY

IMRT optimizes a radiation dose distribution to the patient body in a continuous three-dimensional space. However, space needs to be discretized for the purpose of computation and quality assessment. Conventional approaches apply discretization at the problem definition phase. That is, the space is discretized into voxels and radiation beams are discretized into beamlets. A simple linear model $\vec{d}=B\vec{w}$ is then used throughout the optimization for both objective and derivative evaluations. Voxel and beamlet discretization and the linear model simplify the mathematical formulation for the optimization problem, but do so at the cost of limited modeling power, limited spatial resolution, huge pre-computation demand, and huge memory requirements. In the NVBB framework, IMRT optimization is formulated as a DTPO problem and both dose calculation and derivative evaluation are derived in the continuous space. Flexible discretization is only applied in the final implementation phase. Ray discretization in BEV is a natural representation to its physical counterpart with inherent energy conservation and beam divergence and without any missing points. The NVBB ray tracing method performs both dose calculation and derivative calculation with linear spatial and temporal complexity and with no large pre-computation. "Adaptive full dose correction" combines the advantages of CCCS dose accuracy and FCBB dose efficiency, making the iteration dose approach the full dose and the optimization dose approach the final dose with high fidelity.

Although the examples presented in this document used TomoTherapy® systems and applications to illustrate the NVBB framework, the framework itself is directly applicable to other IMRT modalities, including conventional fixed-beam IMRT and volumetric modulated arc therapy ("VMAT"). In fact, conventional IMRT and VMAT, which each have a larger field size than TomoTherapy®, could take even more advantage of the NVBB framework than TomoTherapy®, where the field size is limited by the jaw width. Therefore, more planning throughput and plan quality gains of conventional IMRT and VMAT would be expected using the NVBB framework instead of the VBS framework.

For simplicity, a single source model was also used for the description of the NVBB framework. While the single source model is sufficient for the flattening-filter-free TomoTherapy® system, it could be less accurate for the conventional linac due to significant head scatters. Therefore, a dual source model could be used in full and final dose calculation, while keeping the single source model only in approximate dose and derivative calculation. Such a scheme would improve the accuracy with a marginal increase in complexity and a marginal change in workflow.

Therefore, a NVBB framework for IMRT optimization has been disclosed. The continuous viewpoint and DTPO nature of the NVBB framework eliminate the need for beamlets, as well as the artifacts associated with voxel and beamlet partitions. The low linear temporal and spatial complexity of the framework enable efficient handling of very large scale IMRT optimization problems by a single workstation without a computer cluster, which saves significantly on hardware and service costs. The GPU implementation of the NVBB framework results in better plan qualities and many-fold improved throughputs, compared with the conventional VBS framework on a computer cluster. In addition, the framework itself is directly applicable to most IMRT modalities. The disclosed NVBB ray tracing can also be used in other applications, such as cone beam CT image reconstruction.

Thus, embodiments of the invention provide, among other things, a non-voxel, broad-beam based algorithm for performing ray tracing and related applications within a radiation treatment environment. Various features and advantages of the invention are set forth in the following claims.

APPENDIX i. Jacobian of the Transformation from the BEV-CS to the Cartesian CS

As one example, the following can be assumed:

$$e_u = e_x, \ e_v = e_y, \text{ and } e_s = e_z \quad (67)$$

because $\{e_u, e_v, e_s\}$ and $\{e_x, e_y, e_z\}$ are congruent by a rotation. The assumption of Equation (67) yields:

$$x = \frac{r}{r_0}u, \ y = \frac{r}{r_0}v \text{ and } z = \frac{r}{r_0}s - s \quad (68)$$

where $r_0 = \sqrt{u^2 + v^2 + s^2}$. The partial derivatives of x can be calculated as:

$$\begin{aligned}
\frac{\partial x}{\partial u} &= \frac{\partial}{\partial u}\left(\frac{r}{r_0}u\right) \\
&= \frac{\partial}{\partial u}\left(\frac{r}{\sqrt{u^2+v^2+s^2}}u\right) \\
&= \frac{r}{\sqrt{u^2+v^2+s^2}} + r \cdot u \cdot \left(-\frac{1}{2}\right)(u^2+v^2+s^2)^{-3/2} \cdot 2u \\
&= \frac{r \cdot (v^2+s^2)}{r_0^3}
\end{aligned} \quad (69)$$

$$\begin{aligned}
\frac{\partial x}{\partial v} &= \frac{\partial}{\partial v}\left(\frac{r}{r_0}u\right) \\
&= \frac{\partial}{\partial v}\left(\frac{r}{\sqrt{u^2+v^2+s^2}}u\right) \\
&= r \cdot u \cdot \left(-\frac{1}{2}\right)(u^2+v^2+s^2)^{-3/2} \cdot 2v \\
&= \frac{-ruv}{r_0^3}
\end{aligned} \quad (70)$$

and $$\frac{\partial x}{\partial r} = \frac{u}{r_0} \quad (71)$$

Similarly, the partial derivatives of y and z are:

$$\frac{\partial y}{\partial u} = \frac{-ruv}{r_0^3}, \ \frac{\partial y}{\partial v} = \frac{r \cdot (u^2+s^2)}{r_0^3}, \ \frac{\partial y}{\partial r} = \frac{v}{r_0} \quad (72)$$

and $$\frac{\partial z}{\partial u} = \frac{-rsu}{r_0^3}, \ \frac{\partial z}{\partial v} = \frac{-rsv}{r_0^3}, \ \frac{\partial z}{\partial r} = \frac{s}{r_0} \quad (73)$$

Hence, the Jacobian is:

$$\begin{bmatrix} \frac{\partial x}{\partial u} & \frac{\partial x}{\partial v} & \frac{\partial x}{\partial r} \\ \frac{\partial y}{\partial u} & \frac{\partial y}{\partial v} & \frac{\partial y}{\partial r} \\ \frac{\partial z}{\partial u} & \frac{\partial z}{\partial v} & \frac{\partial z}{\partial r} \end{bmatrix} = \begin{bmatrix} \frac{r \cdot (v^2+s^2)}{r_0^3} & \frac{-ruv}{r_0^3} & \frac{u}{r_0} \\ \frac{-ruv}{r_0^3} & \frac{r \cdot (u^2+s^2)}{r_0^3} & \frac{v}{r_0} \\ \frac{-rsu}{r_0^3} & \frac{-rsv}{r_0^3} & \frac{s}{r_0} \end{bmatrix} \quad (74)$$

$$= \frac{r^2 s r_0^4}{r_0^7}$$

$$= \frac{r^2 s}{r_0^3}$$

ii. Proof of Accuracy of the Correction-Based Dose Calculation Scheme

Let $\ddot{D}_f$ denote the accurate dose and $\tilde{D}_f$ denote the approximate dose. Both $\ddot{D}_f$ and $\tilde{D}_f$ are linear with respect to the fluence map f (f≧0), and, therefore, can be written as:

$$\ddot{D}_f(x) = (\ddot{B}f)(x) = \int f(u) \ddot{b}(x,u) du \qquad (75)$$

and $$\tilde{D}_f(x) = (\tilde{B}f)(x) = \int f(u)\tilde{b}(x,u)du \qquad (76)$$

Suppose that $\tilde{D}_f$ approximates $\ddot{D}_f$ with first order accuracy. Therefore, there is a small number $\epsilon_2$ such that for any fluence map f and x the following inequality holds:

$$|\ddot{D}_f(x) - \tilde{D}_f(x)| = |((\ddot{B} - \tilde{B})f)(x)| \leq \epsilon_2 \ddot{D}_f(x) \qquad (77)$$

For given fluence maps $f_0$ and f satisfying:

$$|f(u) - f_0(u)| = |\lambda(u)f(u)| \leq \epsilon_1 f(u) \qquad (78)$$

for a small number $\epsilon_1$, the "iteration dose" $D_f(x)$ is defined based on $\tilde{D}_f(x)$ and the correction term $\Delta D_{f_0} = \ddot{D}_{f_0} - \tilde{D}_{f_0}$:

$$D_f(x) = \tilde{D}_f(x) + \Delta D_{f_0}(x) \qquad (79)$$

Proposition $D_f(x)$ approximates $\ddot{D}_f(x)$ with second order accuracy; that is:

$$|\ddot{D}_f(x) - D_f(x)| \leq \epsilon_1 \epsilon_2 \ddot{D}_f(x) \qquad (80)$$

Proof:

$$\begin{aligned}|\ddot{D}_f(x) - D_f(x)| &= |\ddot{D}_f(x) - (\tilde{D}_f(x) + \ddot{D}_{f_0}(x) - \tilde{D}_{f_0}(x))| \\ &= |(\ddot{D}_f(x) - \ddot{D}_{f_0}(x)) - (\tilde{D}_f(x) - \tilde{D}_{f_0}(x))| \\ &= |\ddot{D}_{f-f_0}(x) - \tilde{D}_{f-f_0}(x)| \\ &= |\ddot{D}_{\lambda f}(x) - \tilde{D}_{\lambda f}(x)| \\ &= |(\ddot{B} - \tilde{B})\lambda f| \leq \epsilon_1 \cdot |(\ddot{B} - \tilde{B})f| \leq \\ &\quad \epsilon_1 \cdot \epsilon_2 \cdot \ddot{D}_f(x)\end{aligned} \qquad (81)$$

What is claimed is:

1. A method of calculating a dose distribution for a patient for use in a radiation therapy treatment plan, the method comprising:
   acquiring an image of a volume within the patient;
   defining a radiation source;
   defining a reference plane oriented between the radiation source and the patient;
   generating a radiation therapy treatment plan, the plan including a plurality of rays that extend between the radiation source and the patient volume;
   calculating a three-dimensional dose volume for the patient volume from the plurality of rays that intersect the reference plane without first having to independently calculate a dose distribution on each of the plurality of rays; and
   displaying the three-dimensional dose volume.

2. The method of claim 1, wherein the patient volume is continuous for the calculation of the three-dimensional dose volume for the patient volume.

3. The method of claim 1, wherein the patient volume is non-voxeled for the calculation of the three-dimensional dose volume for the patient volume.

4. The method of claim 1, wherein at least one of the plurality of rays is pyramidal-shaped.

5. The method of claim 1, wherein each of the plurality of rays is defined in a beam-eye-view coordinate system.

6. The method of claim 1, further comprising generating an initial set of machine parameters and wherein calculating the three-dimensional dose volume for the patient volume is based on the initial set of machine parameters.

7. The method of claim 1, wherein calculating the three-dimensional dose distribution includes:
   defining a plurality of points based on the reference plane, the beam-eye-view plane defined by the plurality rays and being perpendicular to a line joining the radiation source and a radiation isocenter and being located a predetermined distance from the radiation source; and
   calculating a dose for each of the plurality of points.

8. The method of claim 7, wherein calculating a dose for each of the plurality of points includes:
   determining a central axis contribution, a divergence correction, and a lateral spread function for a dose at each of the plurality of points, and
   multiplying the central axis contribution, the divergence correction term, and the lateral correction term to determine the dose at each of the plurality of points.

9. The method of claim 7, further comprising interpolating the dose for each of the plurality of points to Cartesian grid points.

10. The method of claim 1, further comprising optimizing the three-dimensional dose volume.

11. The method of claim 10, wherein optimizing the three-dimensional dose volume includes:
   (a) evaluating an objective functional based on the three-dimensional dose volume;
   (b) calculating a first derivative of the objective functional;
   (c) updating the initial set of machine parameters based on the objective functional; and
   (d) repeating acts (a) through (c) at least one time.

12. The method of claim 11, wherein calculating a first derivative of the objective functional includes performing non-voxel, broad-beam based ray tracing.

13. The method of claim 11, wherein repeating acts (a) through (c) at least one time includes repeating act (a) through (c) until the updated set of machine parameters substantially satisfy at least one clinical goal.

14. The method of claim 11, further comprising performing steps (a) through (d) in substantially real-time.

15. The method of claim 10, wherein optimizing the three-dimensional dose volume includes optimizing the three-dimensional dose volume based on at least one machine parameter.

16. The method of claim 15, wherein the at least one machine parameter includes a collimator jaw position.

17. The method of claim 15, wherein the at least one machine parameter includes a collimator leaf position.

18. The method of claim 15, wherein the at least one machine parameter includes at least one of a gantry angle, a gantry speed, a couch position, a couch speed, a leaf open time, and a linac output.

19. A method of optimizing a dose distribution for a patient for use in a radiation therapy treatment plan, the method comprising:
- (a) acquiring an image of a volume within the patient;
- (b) generating a radiation therapy treatment plan, the plan including a plurality of rays that extend between a radiation source and the patient volume;
- (c) generating an initial set of machine parameters;
- (d) calculating a three-dimensional dose volume based on the initial set of machine parameters and the patient volume, the calculation further based on the plurality of rays that intersect the reference plane without first having to independently calculate a dose distribution on each of the plurality of rays;
- (e) evaluating an objective functional based on the three-dimensional dose volume;
- (f) calculating a first derivative of the objective functional;
- (g) updating the initial set of machine parameters based on the objective functional;
- (h) repeating acts (d) through (g) at least one time; and
- (i) displaying the three-dimensional dose volume.

20. The method of claim 19, wherein calculating a first derivative of the objective functional includes performing non-voxel, broad-beam based ray tracing.

21. The method of claim 19, wherein repeating acts (d) through (g) at least one time includes repeating act (d) through (g) until the updated set of machine parameters substantially satisfy at least one clinical goal.

22. The method of claim 19, further comprising performing steps (a) through (h) in substantially real-time.

23. The method of claim 19, wherein the initial set of machine parameters includes a collimator jaw position.

24. The method of claim 19, wherein the initial set of machine parameters includes a collimator leaf position.

25. The method of claim 19, wherein the initial set of machine parameters includes at least one of a gantry angle, a gantry speed, a couch position, a couch speed, a leaf open time, and a linac output.

26. The method of claim 19, wherein the patient volume is continuous for the calculation of the three-dimensional dose volume for the patient volume.

27. The method of claim 19, wherein the patient volume is non-voxeled for the calculation of the three-dimensional dose volume for the patient volume.

28. The method of claim 19, wherein at least one of the plurality of rays is pyramidal-shaped.

29. The method of claim 19, wherein each of the plurality of rays is defined in a beam-eye-view coordinate system.

30. The method of claim 19, wherein calculating the three-dimensional dose distribution includes:
defining a plurality of points based on the reference plane, the beam-eye-view plane defined by the plurality rays and being perpendicular to a line joining the radiation source and a radiation isocenter and being located a predetermined distance from the radiation source; and
calculating a dose for each of the plurality of points.

31. The method of claim 30, wherein calculating a dose for each of the plurality of points includes:
determining a central axis contribution, a divergence correction, and a lateral spread function for a dose at each of the plurality of points, and
multiplying the central axis contribution, the divergence correction term, and the lateral correction term to determine the dose at each of the plurality of points.

32. The method of claim 30, further comprising interpolating the dose for each of the plurality of points to Cartesian grid points.

* * * * *